United States Patent [19]

Nicholas et al.

[11] Patent Number: 5,514,157
[45] Date of Patent: May 7, 1996

[54] ARTICULATING ENDOSCOPIC SURGICAL APPARATUS

[75] Inventors: David A. Nicholas, Trumbull; Ernie Aranyi, Easton, both of Conn.; Boris Zvenyatsky, Bronx, N.Y.; Paul A. Matula, Brookfield, Conn.; Stanley H. Remiszewski, Bolton, Mass.; David T. Green, Wesport; Henry Bolanos, East Norwalk, both of Conn.

[73] Assignee: United States Surgical Corporation, Norwalk, Conn.

[21] Appl. No.: 413,493

[22] Filed: Mar. 31, 1995

Related U.S. Application Data

[63] Continuation of Ser. No. 925,496, Sep. 4, 1992, abandoned, which is a continuation-in-part of Ser. No. 834,687, Feb. 12, 1992, Pat. No. 5,383,888.

[51] Int. Cl.⁶ ............................. A61B 1/00; A61B 17/02; A61B 17/28
[52] U.S. Cl. ...................... 606/206; 606/205; 606/198; 606/201; 606/204
[58] Field of Search ................................... 600/201, 204, 600/214; 606/205, 206, 207, 208, 191, 198; 604/105, 106; 128/751

[56] References Cited

U.S. PATENT DOCUMENTS

| | | |
|---|---|---|
| 1,620,828 | 3/1927 | Molony . |
| 2,028,635 | 1/1936 | Wappler . |
| 2,113,246 | 4/1938 | Wappler . |
| 3,144,020 | 8/1964 | Zingale . |
| 3,788,303 | 1/1974 | Hall . |
| 3,877,433 | 4/1975 | Librach . |
| 3,892,228 | 7/1975 | Mitsui . |
| 4,000,743 | 1/1977 | Weaver . |
| 4,022,208 | 5/1977 | Valtchev . |
| 4,430,076 | 2/1984 | Harris . |
| 4,763,669 | 8/1988 | Jaeger . |

(List continued on next page.)

FOREIGN PATENT DOCUMENTS

| | | |
|---|---|---|
| 0165472 | 12/1985 | European Pat. Off. . |
| 0405250 | 1/1991 | European Pat. Off. . |
| 0412282 | 2/1991 | European Pat. Off. . |
| 0449663 | 10/1991 | European Pat. Off. . |
| 0484671 | 5/1992 | European Pat. Off. . |
| 2469912 | 11/1979 | France . |
| 3303335 | 8/1984 | Germany . |
| 8535164 | 4/1986 | Germany . |
| 8711051 | 2/1988 | Germany . |
| 8808285 | 9/1988 | Germany . |
| 9007356 | 6/1991 | Germany . |
| 9109097 | 10/1991 | Germany . |
| 9300161 | 4/1993 | Germany . |
| 736949 | 7/1977 | U.S.S.R. . |
| 1360708 | 12/1987 | U.S.S.R. . |

OTHER PUBLICATIONS

European Search Report for EP Appln. No. 93 11 2520.
European Search Report for EP Appln. 93 10 2141.
Richard Wolf, "For Fixation and Elevation of the Uterus", 1989.
Instruction Manual for Uterine Mobilizer.
Stephen L. Corson, M.D., "Two New Laparoscopic Instruments: Bipolar Sterilizing Forceps and Uterine Manipulator," Medical Instrumentation, vol. 11, No. 1, Jan.–Feb. 1977.

(List continued on next page.)

Primary Examiner—Richard J. Apley
Assistant Examiner—Beverly M. Flanagan

[57] ABSTRACT

A surgical instrument is provided for use in endoscopic or laparoscopic procedures. The instrument includes a handle portion, an endoscopic portion extending from the handle portion, an articulating section pivotably connected to a distal end portion of the endoscopic portion, and a retractor assembly operatively associated with the articulating section. Structure is provided for manipulating the articulating section relative to the longitudinal axis of the endoscopic portion within an angular degree of rotation. An injection port may also be provided to deliver fluids through the endoscopic portion to the operative site.

22 Claims, 21 Drawing Sheets

U.S. PATENT DOCUMENTS

| | | | |
|---|---|---|---|
| 4,872,456 | 10/1989 | Hasson | 606/207 |
| 4,880,015 | 11/1989 | Nierman. | |
| 4,941,455 | 7/1990 | Watanabe et al.. | |
| 4,944,741 | 7/1990 | Hasson. | |
| 4,947,827 | 8/1990 | Opie et al.. | |
| 4,950,273 | 8/1990 | Briggs. | |
| 5,104,377 | 4/1992 | Levine. | |
| 5,131,382 | 7/1992 | Meyer. | |
| 5,135,524 | 8/1992 | Bonnet. | |
| 5,152,279 | 10/1992 | Wilk. | |
| 5,178,133 | 1/1993 | Pena | 604/105 X |
| 5,195,505 | 3/1993 | Josefsen | 606/198 X |
| 5,195,506 | 3/1993 | Hulfish | 128/20 |
| 5,199,419 | 4/1993 | Remiszewski et al.. | |
| 5,209,747 | 5/1993 | Knoepfler | 606/205 X |
| 5,235,966 | 8/1993 | Jamner. | |
| 5,237,985 | 8/1993 | Hodgson et al.. | |
| 5,245,987 | 9/1993 | Redmond et al. | 128/20 |

OTHER PUBLICATIONS

"Jarit Instrument Update", Jamner Surgical Instruments, Inc., Oct. 1991.

"Nanticoke™ Advanced Laparoscopic/Thoracoscopic Instruments For The Nest Generation of Endoscopic Surgery," Cabot Medical Corporation, Jan. 1992.

"Advanced Laparoscopy," Snowden–Pencer, Apr. 1992.

"Manual Instruments", Cooper Endoscopy, Oct. 1992.

Optik Incorporated, *Surgical Products*, p. 33, Jun. 1992 edition.

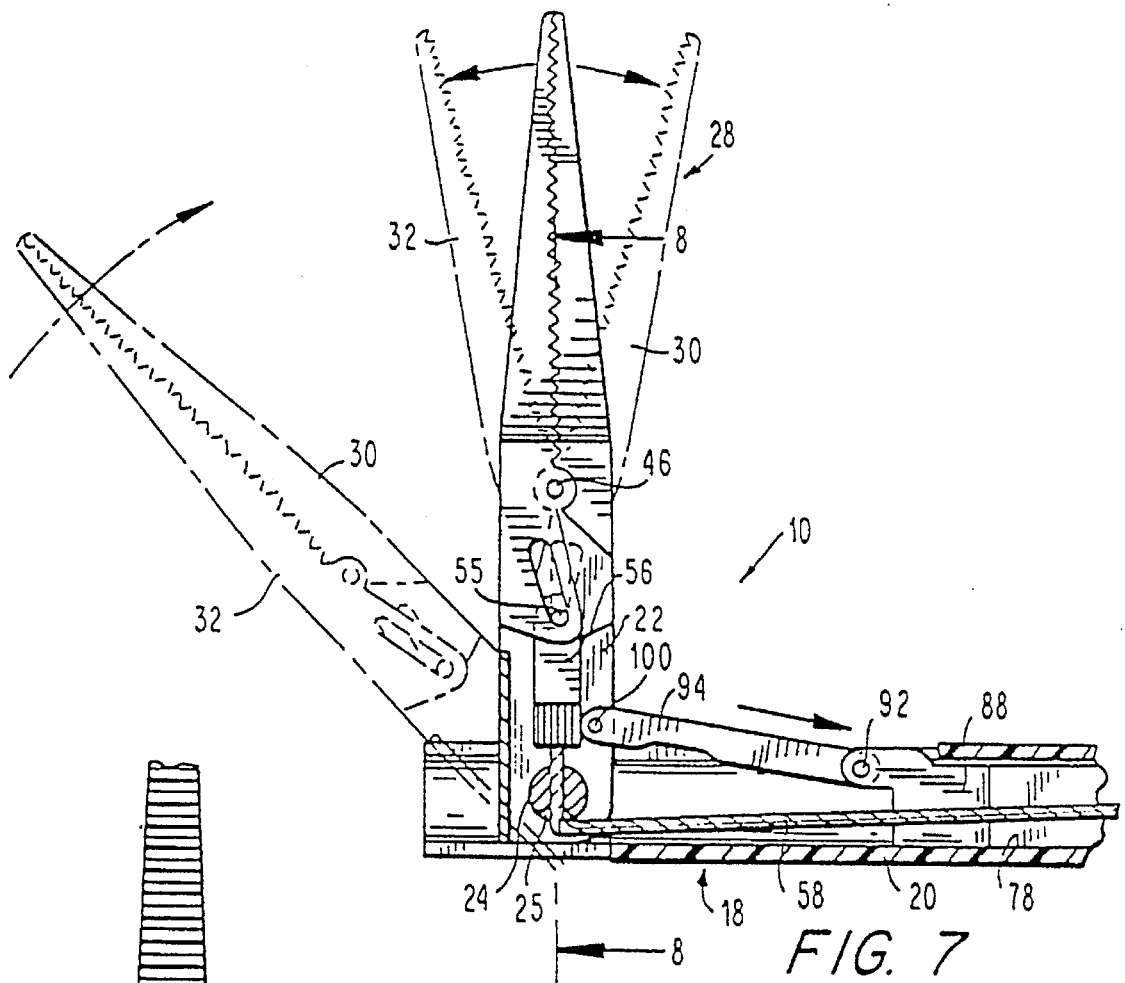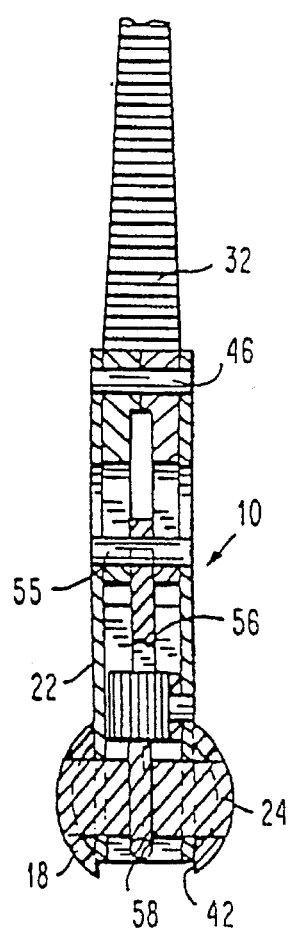
FIG. 7
FIG. 8

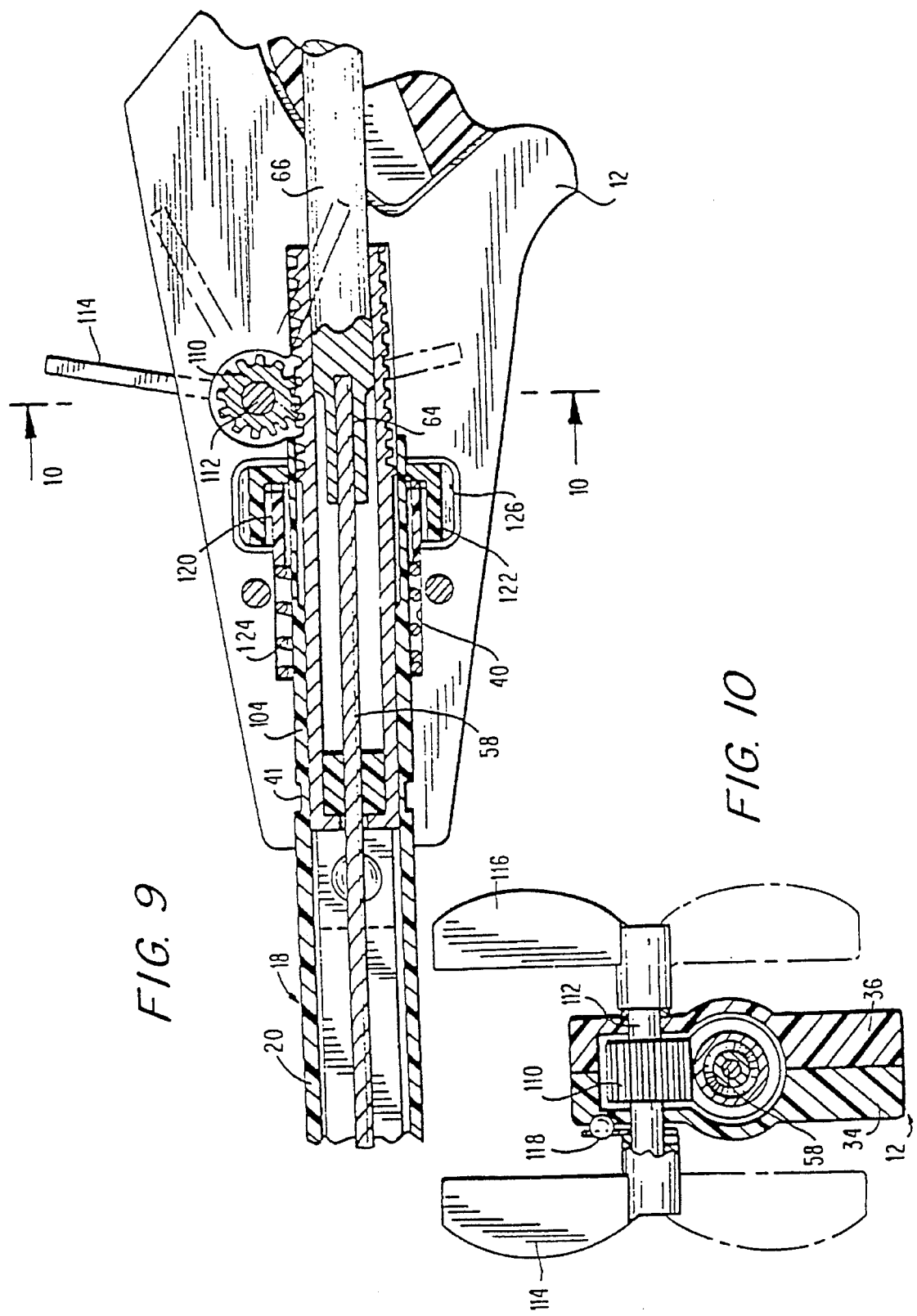

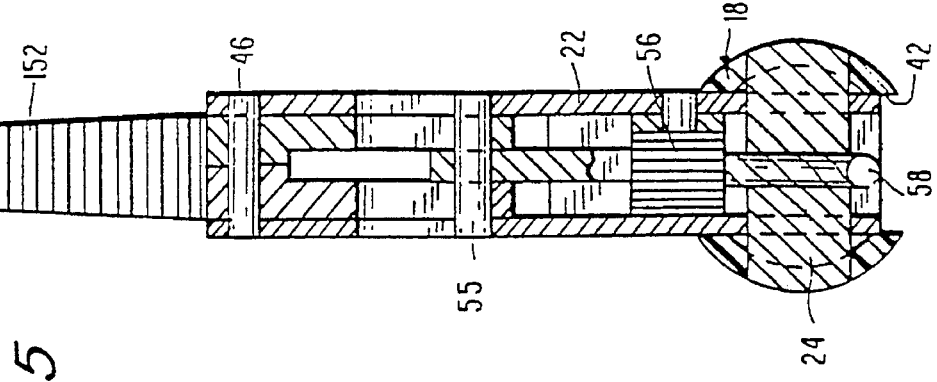
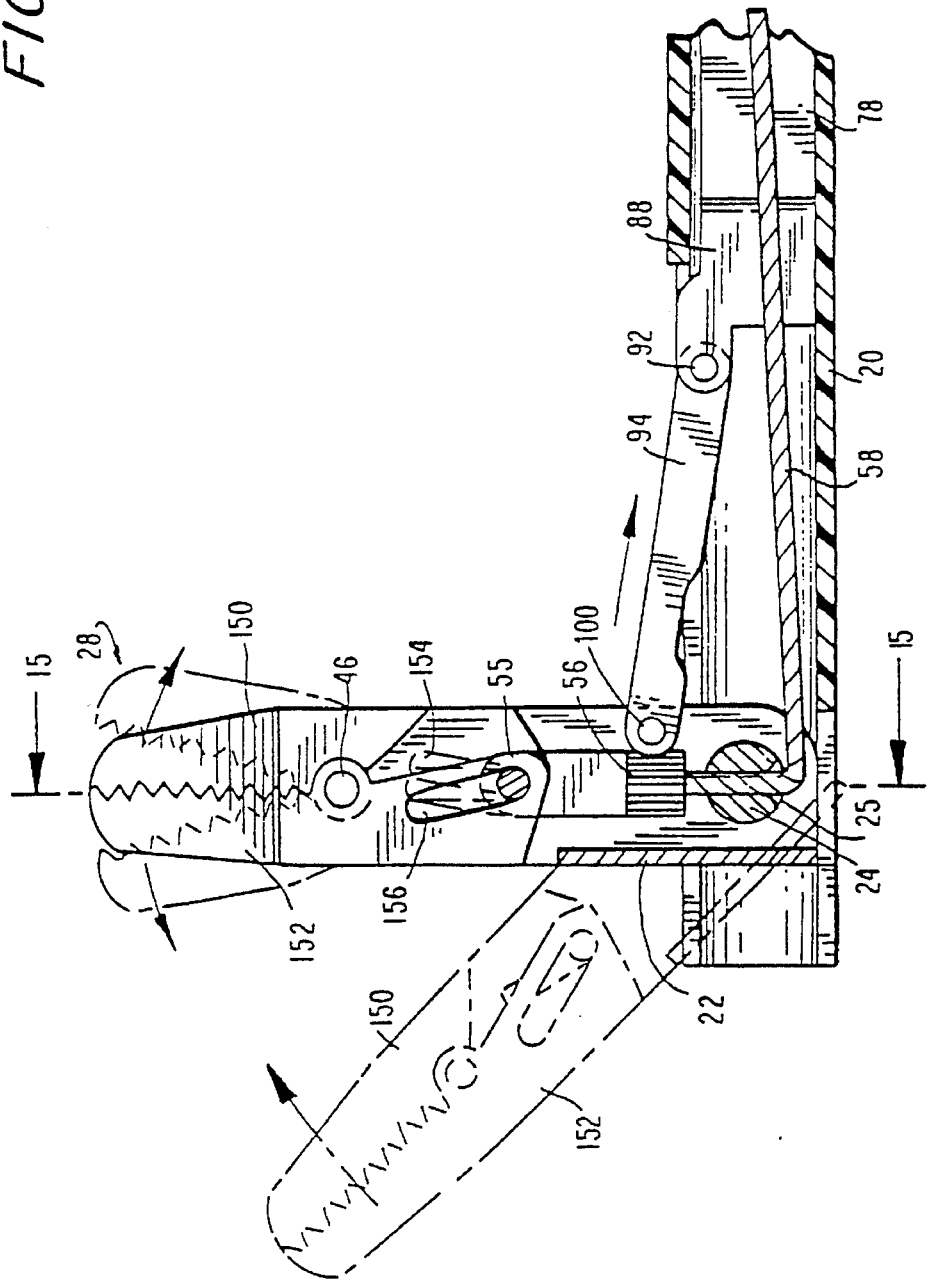
FIG. 15
FIG. 14

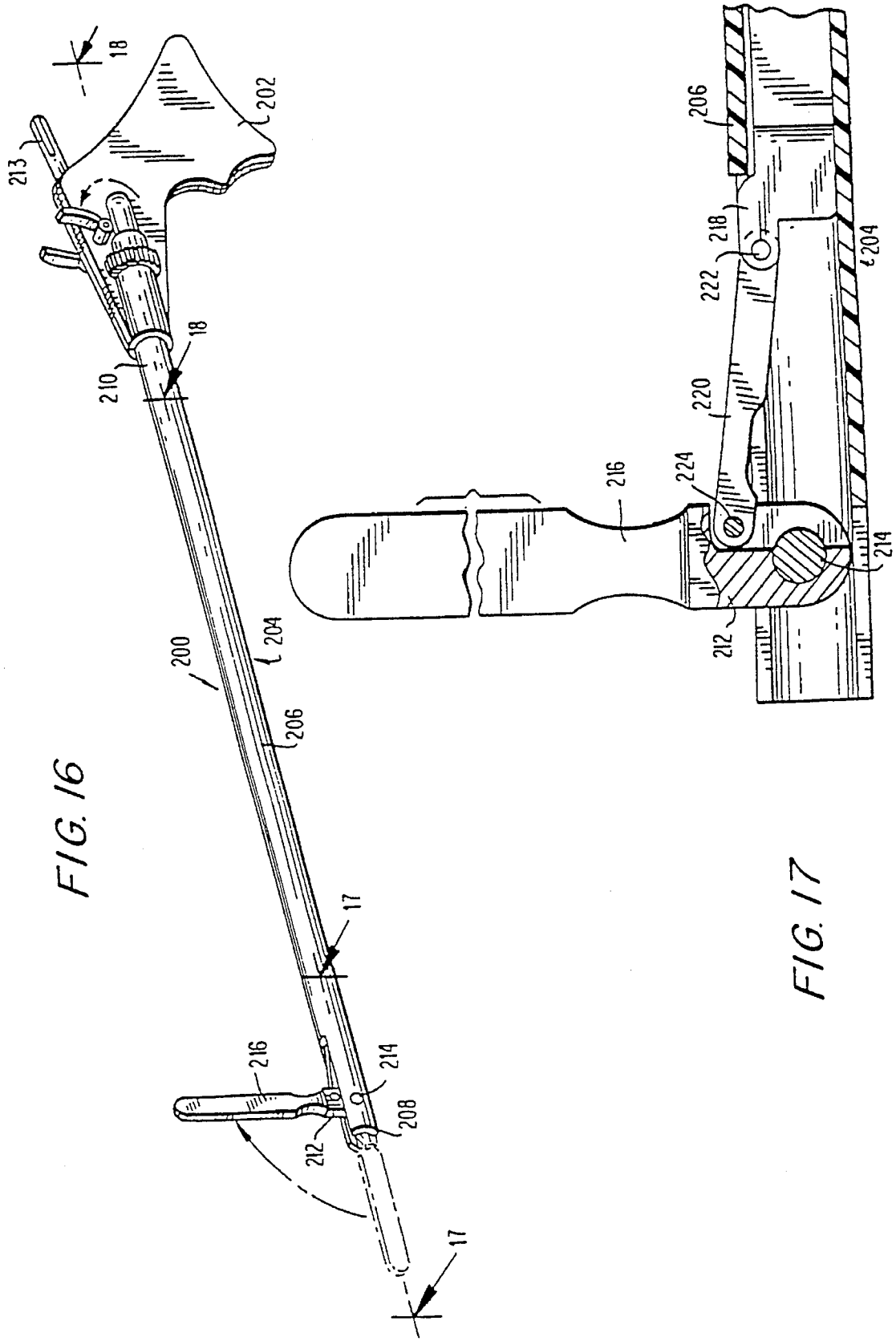

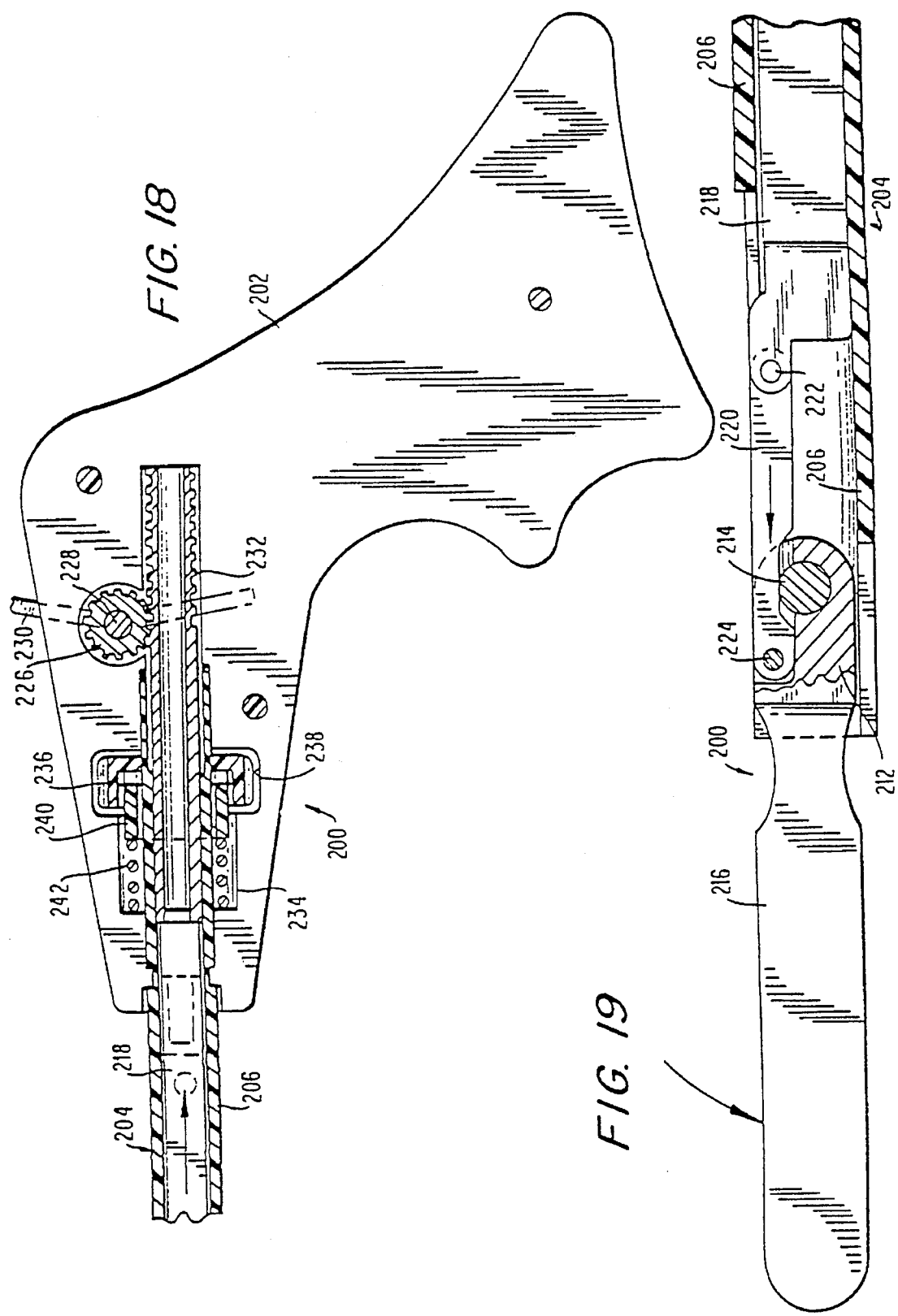

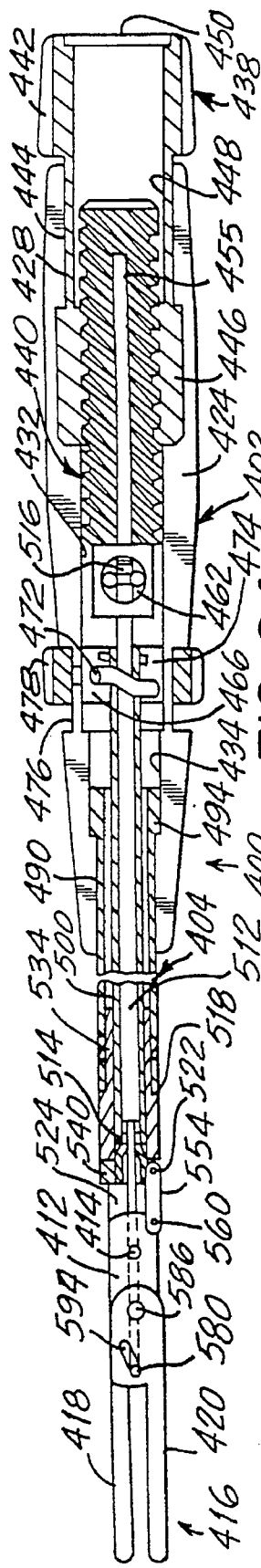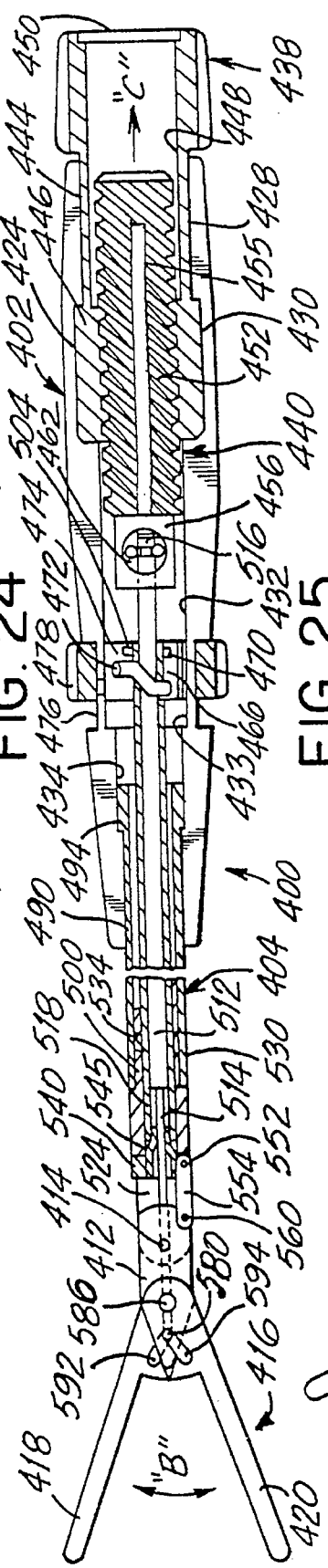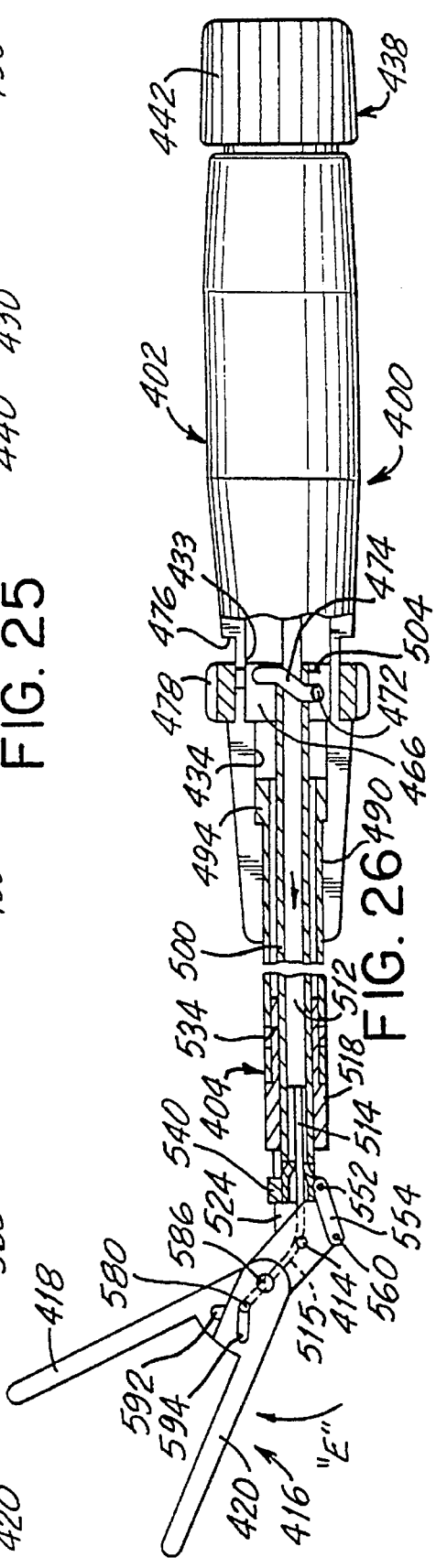

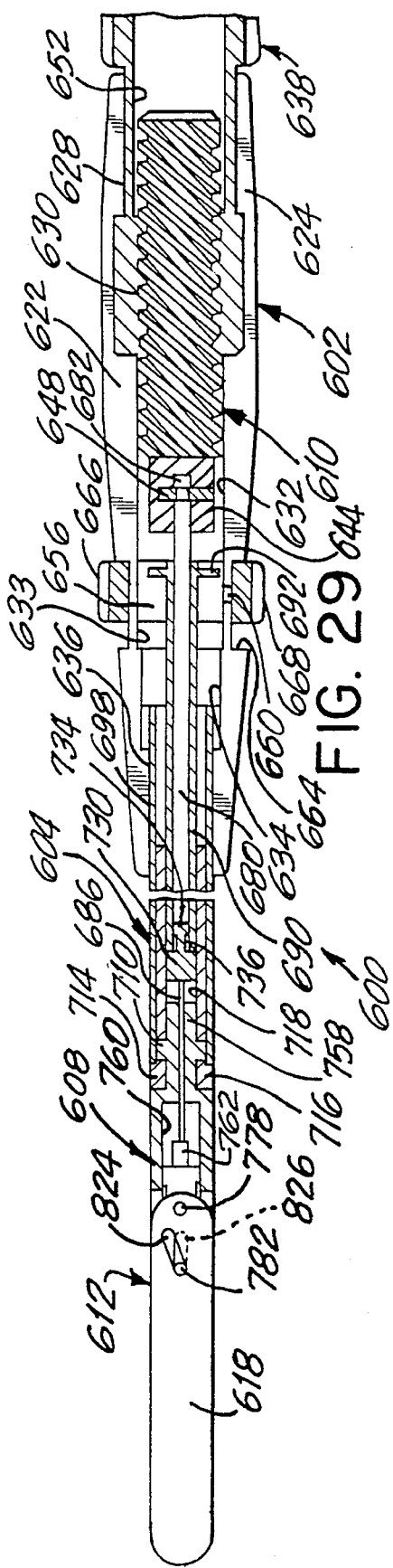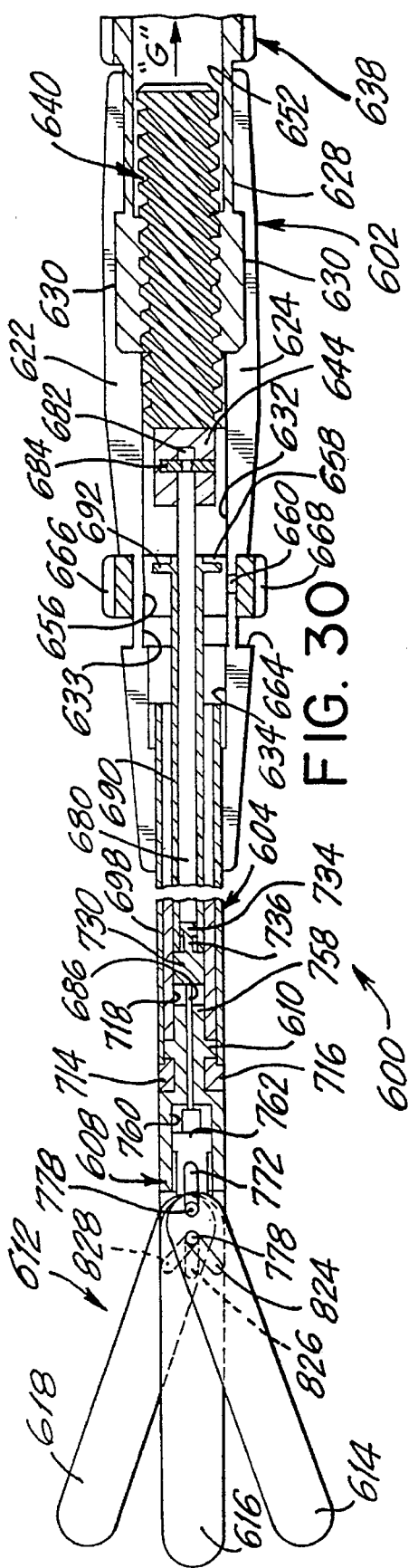

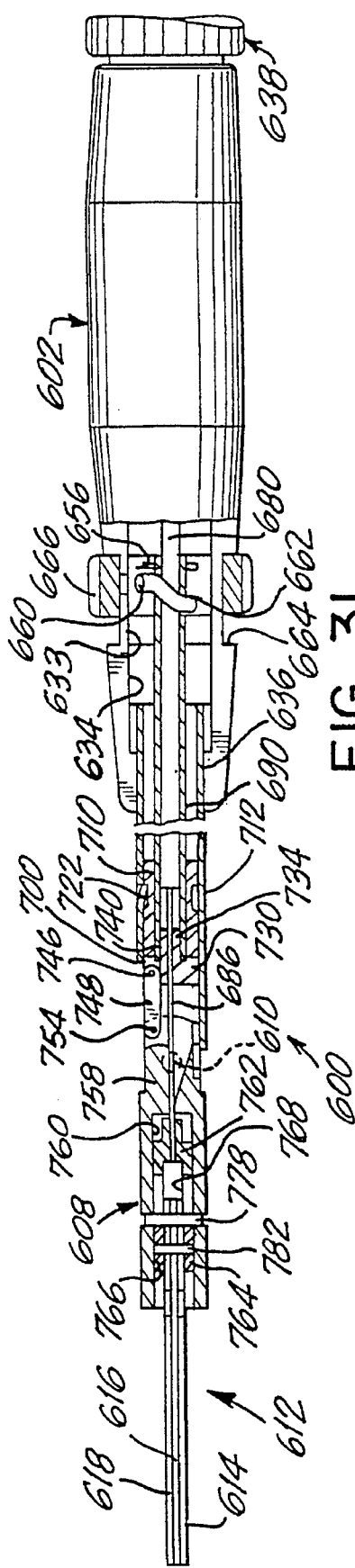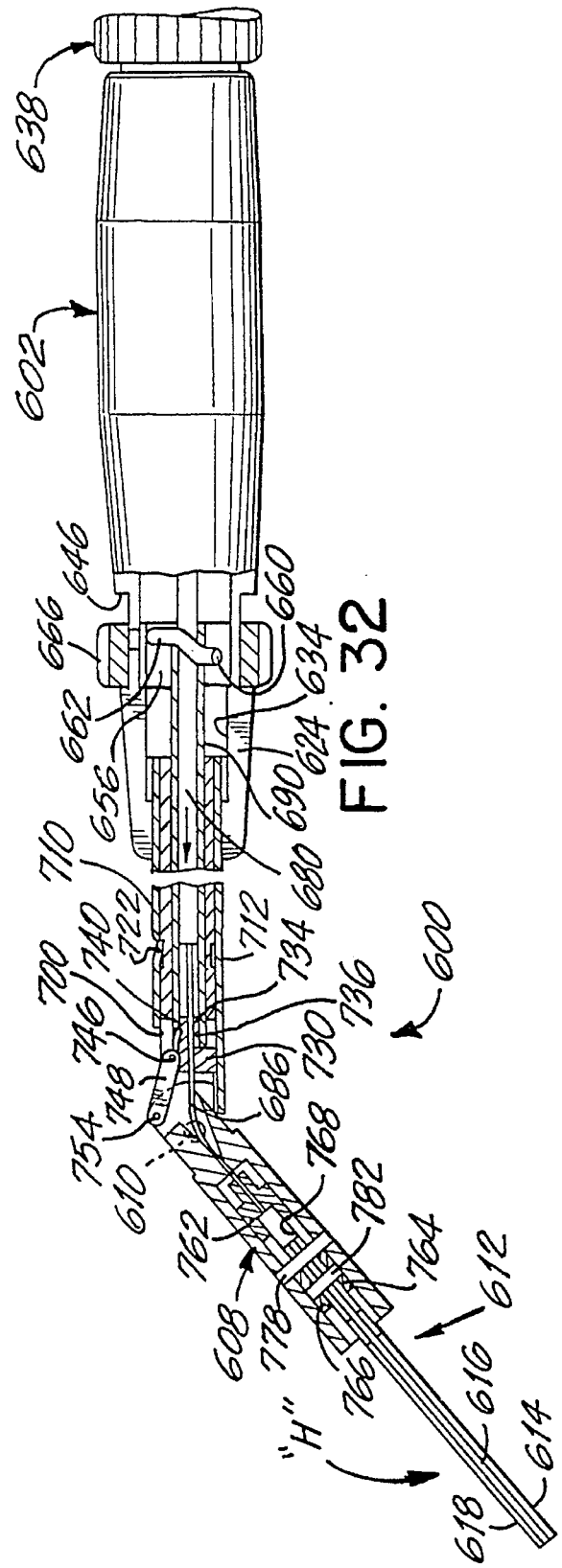

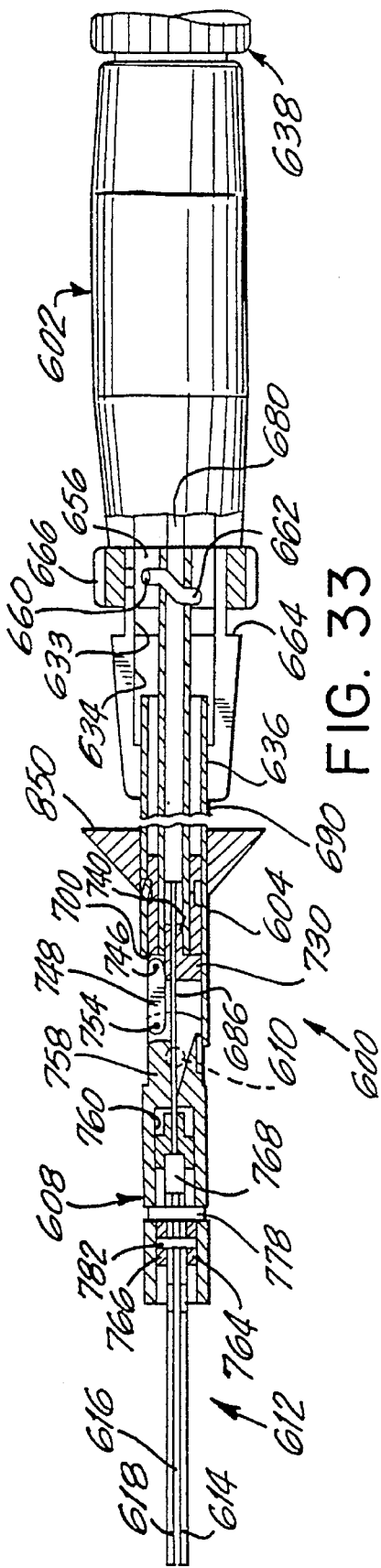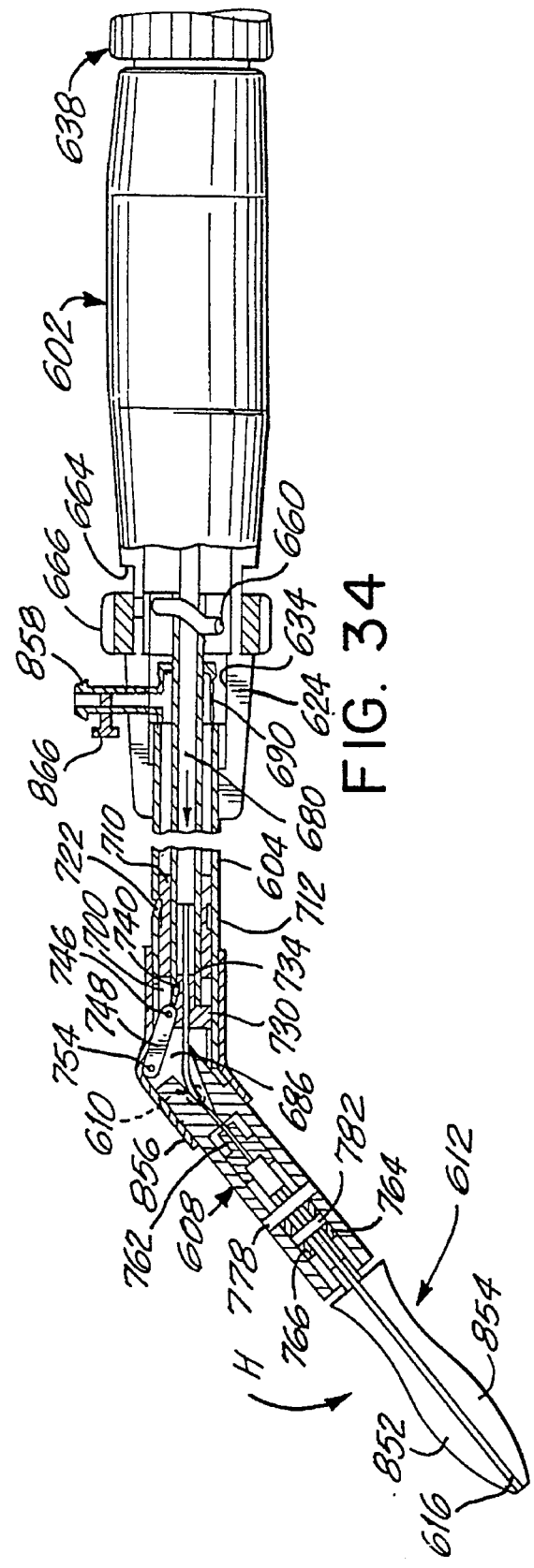

ARTICULATING ENDOSCOPIC SURGICAL APPARATUS

CROSS-REFERENCE TO RELATED APPLICATION

This is a continuation, of appln. Ser. No. 07/925,496 filed on Sep. 4, 1992, abandoned, which is a continuation-in-part of appln. Ser. No. 07/834,687 filed Feb. 12, 1992, now U.S. Pat. No. 5,383,888.

BACKGROUND OF THE INVENTION

1. Field of the Invention

The subject invention relates to surgical apparatus for performing laparoscopic and endoscopic surgical procedures, and more particularly to apparatus having an end portion which can be articulated in a patient's body during a surgical procedure.

2. Description of Related Art

In laparoscopic and endoscopic surgical procedures a small incision or puncture is made in the patient's body to provide access for a tube or cannula device. Once extended into the patient's body, the cannula allows insertion of various surgical instruments such as scissors, dissectors or retractors to perform the surgery.

An example of an endoscopic surgical instrument is illustrated in U.S. Pat. No. 2,113,246 which issued to Wappler on Apr. 5, 1938. This patent discloses endoscopic forceps comprising an elongated conduit with jaws at the distal end thereof, a control rod in the conduit for controlling the operation of the jaws, and a control handle at the proximal end of the conduit which is operatively connected to the control rod. This surgical instrument is extremely limited in its applications in that the angle of the conduit portion mounting the jaws cannot be adjusted in relation to the remaining portion of the conduit during a surgical procedure.

Improvements have been made in the art of surgical instruments to increase their range of operability. For example, U.S. Pat. No. 4,763,669 which issued to Jaeger on Aug. 16, 1988 discloses a microsurgery instrument with an adjustable angle of operation for obtaining cervical biopsies.

Similarly, U.S. Pat. No. 4,880,015 which issued to Nierman on Nov. 14, 1989 discloses a surgical device having an increased range of operability. In particular, this patent shows a biopsy forceps designed for use through a flexible fiberoptic bronchoscope. The biopsy forceps includes a handle connected to a thin elongated flexible shaft with a distal portion thereof hinged to the shaft. A grasping tool or biopsy forceps attached to the distal hinged portion. Control wires extended from the handle to the distal end tot the shaft for controlling the angular rotation of the distal portion of the instrument.

Of the references discussed above, none of these instruments disclose a laparoscopic instrument for insertion into the body cavity through a cannula and adapted for a wide range of laparoscopic surgical applications. Further, the instruments disclosed therein are not provide with means for rotating the tool head about the longitudinal axis of the endoscopic portion of the instrument. Instead, a surgeon using either of these prior art instruments must physically rotate the entire instrument in order to change the rotational orientation of the distal end of the conduit or tube.

Accordingly, it is an object of the subject invention to provide an endoscopic surgical instrument having a tool head which is independently moveable about two axes of rotation relative to the handle while the instrument is in use.

It is another object of the subject invention to provide a lightweight endoscopic surgical instrument which can provide a clearer line of sight for a surgeon during a surgical procedure.

It is still another object of the subject invention to provide an endoscopic surgical instrument in which a wide variety of different tool heads may be employed.

It is yet another object of the subject invention to provide an endoscopic surgical instrument which may be used to perform electrocauterization during surgical procedures.

A further object of the subject invention is to provide an endoscopic surgical instrument which may be used for performing retraction, grasping or dissecting tasks during gynecological procedures.

Another object of the subject invention is to provide an endoscopic surgical instrument for performing retraction, grasping or dissecting tasks during abdominal surgery.

Another object of the subject invention is to provide endoscopic surgical instrument which is inexpensive to manufacture.

These and other objects of the subject invention will be made more apparent from the following description taken in conjunction with the accompanying drawings.

SUMMARY OF THE INVENTION

An endoscopic surgical instrument is disclosed for use in a wide variety of roles including grasping, dissecting, clamping, or retracting materials or tissue during surgical procedures performed within a patient's body and particularly within the abdominal cavity.

The surgical instrument of the subject invention includes a handle portion having a fixed handle, and an endoscopic portion which depends from the handle portion. The endoscopic portion includes an elongated tubular section and an articulating section which is pivotally connected adjacent to the distal end of the tubular section. Tool means are operatively connected to the articulating section of the endoscopic portion. A linkage mechanism is associated with the endoscopic portion of the instrument for selectively pivoting the articulating section in an angular plane relative to the longitudinal axis of the tubular section within about a 90° sector of rotation. This linkage mechanism is preferably controllable form the handle portion of the instrument.

In one embodiment of the subject invention, the surgical instrument may include a handle portion having a fixed handle and a pivoting handle. A cable extends from the pivoting handle through the endoscopic portion to the tool means. In this embodiment, the tool means may comprise a pair of cooperating jaws, the movement of which is controlled by operating the pivoting handle.

The linkage mechanism for pivoting the articulating section of the endoscopic portion preferably may include an elongated push rod extending from the handle portion, through the endoscopic portion. The push rod wold be connected to a link member, which, in turn may be pivotally connected to the articulating section of the endoscopic portion. In addition, the linkage mechanism may include a reciprocating member having a gear rack disposed adjacent to the handle portion of the instrument in cooperation with the proximal end of the elongated push rod. The gear rack member would be movable in an axial direction in response to rotation of an annular pinion gear in the handle portion of the instrument. Rotation of the pinion gear would cause the gear rack member to translate coaxially, causing the push rod to move, and thereby causing the articulating section of the endoscopic portion to pivot within 90° sector of rotation relative to the longitudinal axis of the endoscopic portion of the instrument.

Preferred embodiments of the subject invention may also include means for rotating the endoscopic portion of the surgical instrument about the longitudinal axis thereof. In this instance, an annular bushing, which may be concentrically disposed within an annular cuff, would be provided in the handle portion of the instrument. The proximal end of the endoscopic portion of the instrument would be arranged within the bushing and would be rotatable about its longitudinal axis by rotating the annular cuff.

In another embodiment of the subject invention, the surgical instrument may include a handle portion configured as a pistol-grip and an endoscopic portion including an elongated fixed tubular section which depends from the handle portion and an articulating section pivotally connected to the fixed section adjacent the distal end thereof. An elongated paddle tool would depended from the articulating section of the endoscopic portion for performing retraction tasks during surgical procedures. In addition, a linkage mechanism would then be associated with the endoscopic portion of the instrument for pivoting the articulating section relative to the longitudinal axis of the fixed section, with a 90° sector of rotation. The instrument could also be provided with means for rotating the endoscopic portion thereof about its longitudinal axis.

In yet another embodiment of the subject invention, the surgical instrument includes an axial handle portion from which extends an elongated endoscopic portion having an articulating distal section. A retractor assembly is operatively associated with the articulating section and may include a pair of cooperating retractor rod members or alternatively, a plurality of interleaved retractor blade members. In both instances, the retractor assembly is manipulated between a closed position and an open position by driving assembly housed in the handle portion of the instrument.

The driving assembly includes a rotatable knob member which is threadably connected to an axially advanceable screw member. Rotation of the knob member will cause corresponding axial movements of the screw member relative to the handle portion. This arrangement also permits controlled deployment of the retractor rods or interleaved retractor blades into a variety of intermediate positions between the open and closed position depending upon the specific retraction task at hand. Connective means extend from the screw member to the retractor assembly for translating the axial movement of the driving assembly to the retractor assembly. Also, in both instances, the articulating section of the endoscopic portion of the surgical instrument is manipulated within an angular degree of rotation by a camming assembly which is associated with the handle portion thereof. The camming assembly includes a cam member which is movable between a proximal position and a distal position with respect to the handle portion of the instrument. Linkage means interconnects the cam member with the retractor assembly for translating axial movement of the cam member to the retractor assembly.

Further features of the subject invention will become more readily apparent from the following detailed description of the invention taken in conjunction with accompanying drawings.

BRIEF DESCRIPTION OF THE DRAWINGS

Preferred embodiments of the subject invention will be described hereinbelow with reference to the drawings, wherein:

FIG. 7 is a side cross-sectional view showing, in solid and in phantom lines, the various pivoting movements of the articulating section of the endoscopic portion of the surgical instrument shown in FIG. 1;

FIG. 8 is an enlarged side cross-sectional view of the distal end of the endoscopic surgical instrument taken along line 8—8 of FIG. 7;

FIG. 9 is an enlarged side cross-sectional view of the distal end of the endoscopic surgical instrument illustrating the various positions of the pinon gear which comprises a portion of the linkage mechanism of the subject invention;

FIG. 10 is a front cross-sectional view taken along line 10—10 of FIG. 9;

FIG. 14 is a side cross-sectional view showing, in a solid and in phantom lines the pivotal movements of the articulating section of the endoscopic portion of the subject invention with the alternate embodiment of the tool head shown in FIGS. 11–13;

FIG. 15 is a front cross-sectional view taken along line 15—15 of FIG. 14;

FIG. 16 is a perspective view of an alternate embodiment of the subject invention which includes an articulating paddle for performing retraction tasks;

FIG. 17 is a side cross-sectional view taken along line 17—17 of FIG. 16;

FIG. 18 is a side cross-sectional view taken along line 18—18 of FIG. 16;

FIG. 19 is a side cross-sectional view taken along line 17—17 of FIG. 16;

FIG. 24 is a side cross-sectional view of the endoscopic surgical instrument of FIG. 22 with the retractor assembly thereof in a closed position;

FIG. 25 is a side cross-sectional view of the endoscopic surgical instrument of FIG. 22 with the retractor assembly thereof in an open position;

FIG. 26 is a side cross-sectional view of the endoscopic surgical instrument of FIG. 22 with the distal end portion thereof disposed in an articulated position;

FIG. 29 is a top cross-sectional view of the articulating endoscopic surgical instrument of FIG. 27 with the retractor assembly thereof in a closed position;

FIG. 30 is a top cross-sectional view of the articulating endoscopic instrument of FIG. 27 with the retractor assembly thereof in an opened position;

FIG. 31 is a side cross-sectional view of the articulating endoscopic instrument of FIG. 27;

FIG. 32 is a side cross-sectional view of the articulating endoscopic surgical instrument of FIG. 27 with the distal end portion thereof disposed in an articulated position;

FIG. 33 is a side cross-sectional view of an endoscopic surgical instrument of the present invention equipped with a removable cervix seal; and FIGS. 34 and 35 are side cross-sectional views of an endoscopic surgical instrument of the present invention having fluid injection structure and an articulating sleeve cover.

DETAILED DESCRIPTION OF THE PREFERRED EMBODIMENT

Figure 1:
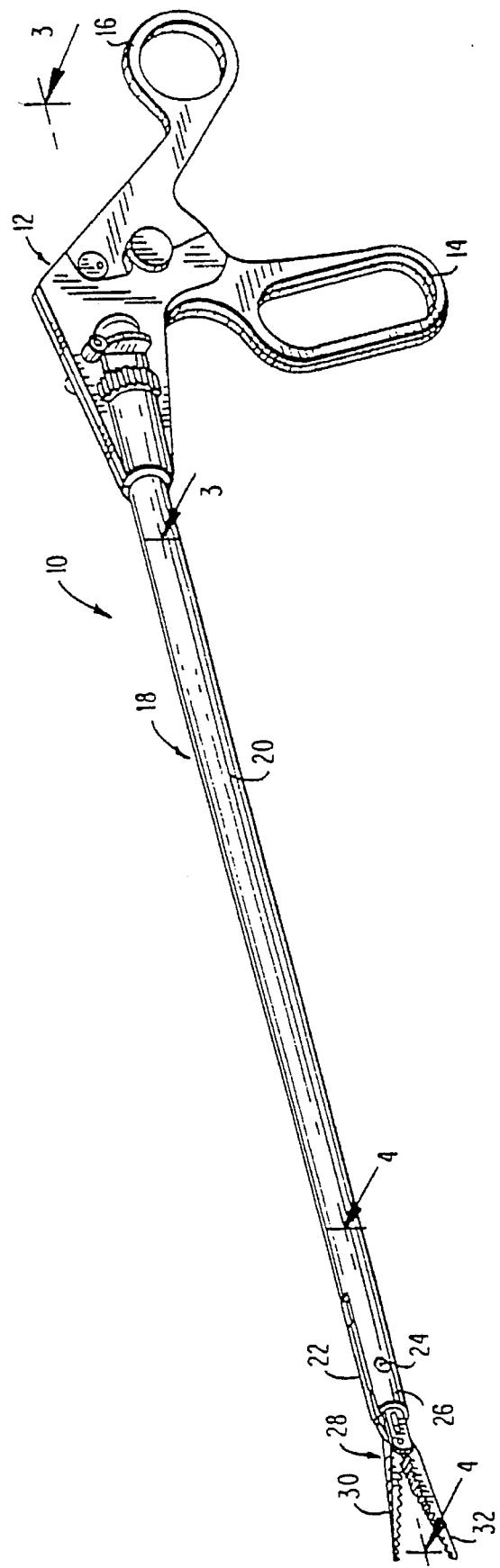
FIG. 1 is a perspective view of an articulating endoscopic surgical instrument in accordance with a preferred embodiment of the subject invention.

The articulating endoscopic surgical instrument of the subject invention is illustrated in FIG. 1 and is designated generally by reference numeral 10. Surgical instrument 10 comprises a handle portion 12 including a fixed handle 14 and a pivoting handle 16. An endoscopic portion 18 extends orthogonally from handle portion 12 and includes an elongated fixed tubular section 20 and an articulating section 22. The articulating section 22 is pivotally connected to the fixed section 20 by a pin 24 disposed adjacent the distal end 26 of section 22. A tool head 28 having cooperating jaws 30, 32 depends from the articulating section 22 and may be formed in a wide variety of configurations including graspers, dissectors, or clamps.

Figure 2:
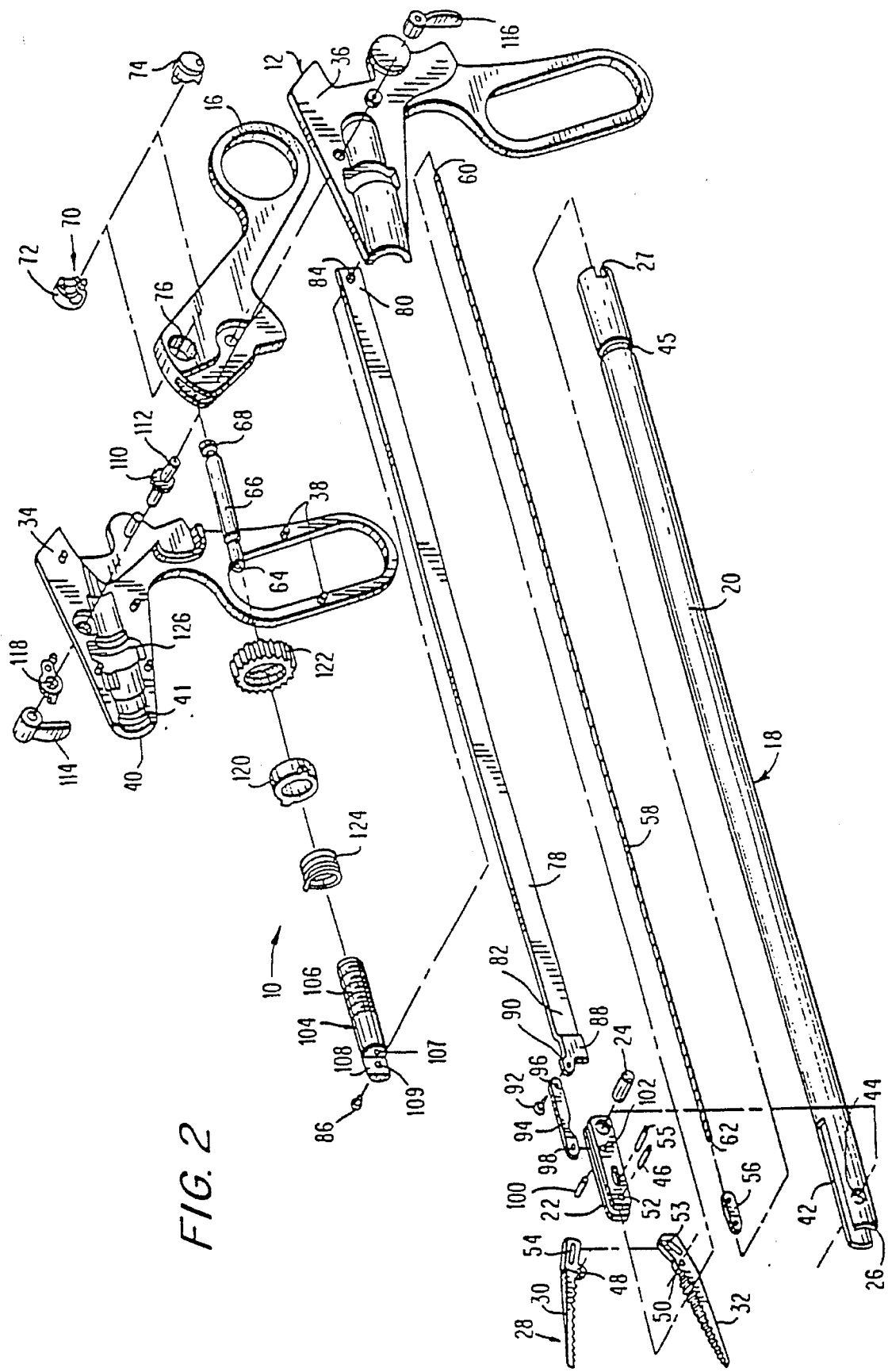
FIG. 2 is an exploded view of the articulating endoscopic surgical instrument of FIG. 1.

Turning to FIG. 2, the handle portion 12 and the associated fixed handle 14 comprises complimentary sections 34 and 36 which are mounted to one another by a plurality of bosses 38 formed on section 34. The plurality of bosses 38 are arranged for engagement in corresponding apertures (not shown), which are formed in section 36 of handle portion 12. In addition, each of the complimentary sections 34, 36 of handle portion 12 are formed with a portion of a stepped bore 40 which is provided therein for accommodating various components of the subject invention, all of which will be described in greater detail hereinbelow. Stepped bore 40 includes a circumferential flange 41 for securing the tubular section 20 of endoscopic portion 18 in handle portion 12.

Figure 4:
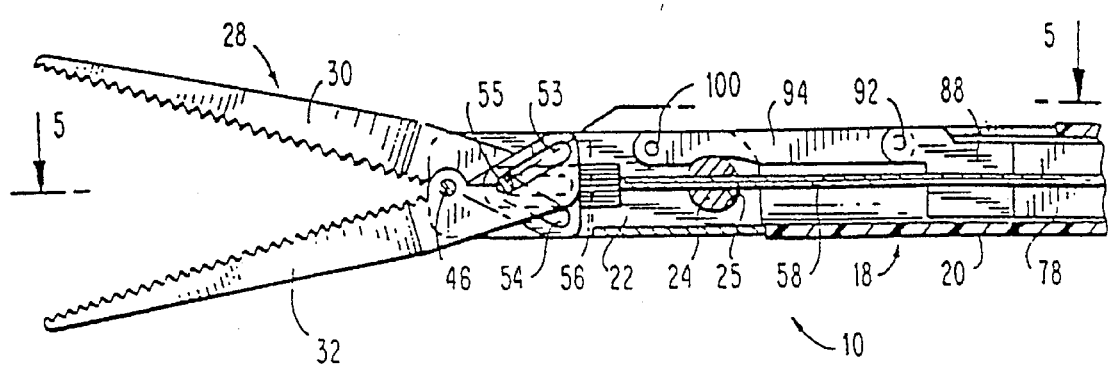
FIG. 4 is a side cross-sectional view taken along line 4—4 of FIG. 1 illustrating the distal end of the endoscopic surgical instrument.
Figure 5:
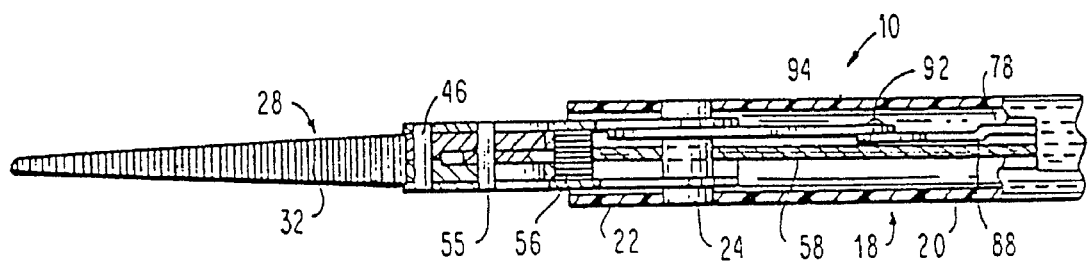
FIG. 5 is a top plan view cross-section view taken along line 5—5 of FIG. 4.
Figure 6:
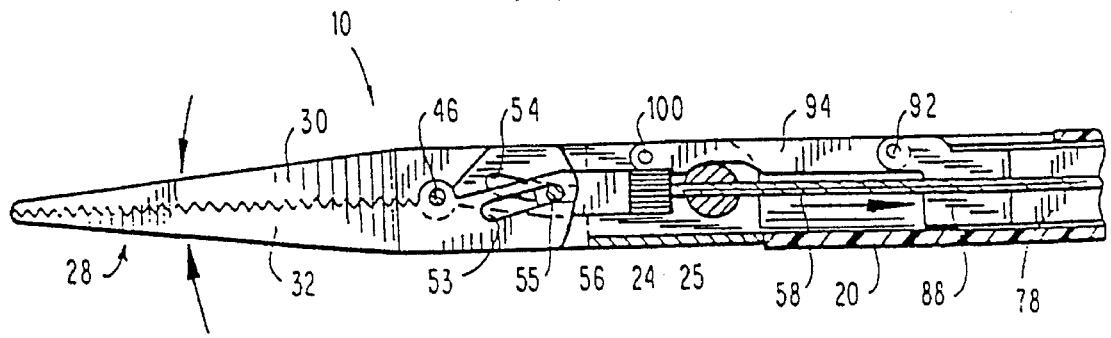
FIG. 6 is a side cross-sectional view of the distal end of the endoscopic surgical instrument showing the jaws in a closed position.
Figure 11:
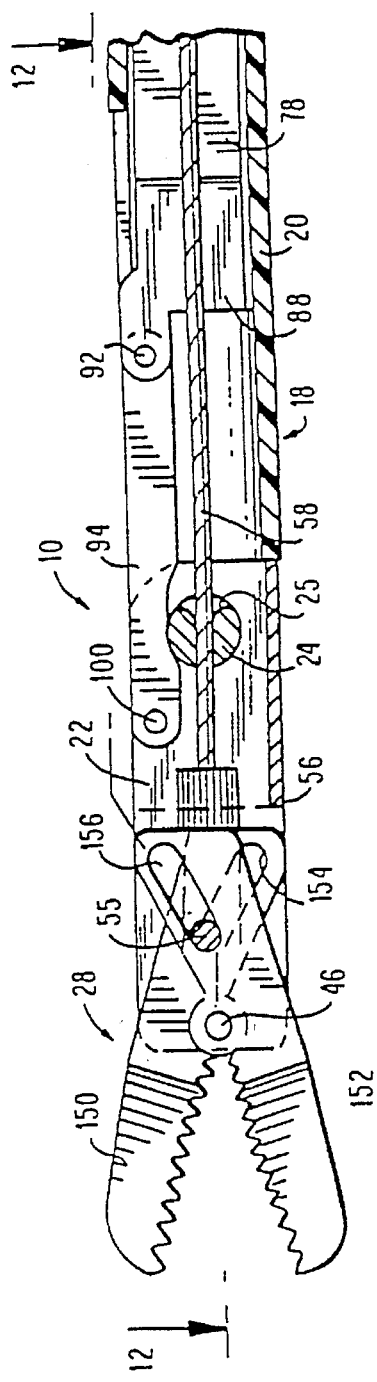
FIG. 11 is a side cross-sectional view illustrating an alternative embodiment of the tool head of the endoscopic surgical instrument of the subject invention in an open position.
Figure 12:
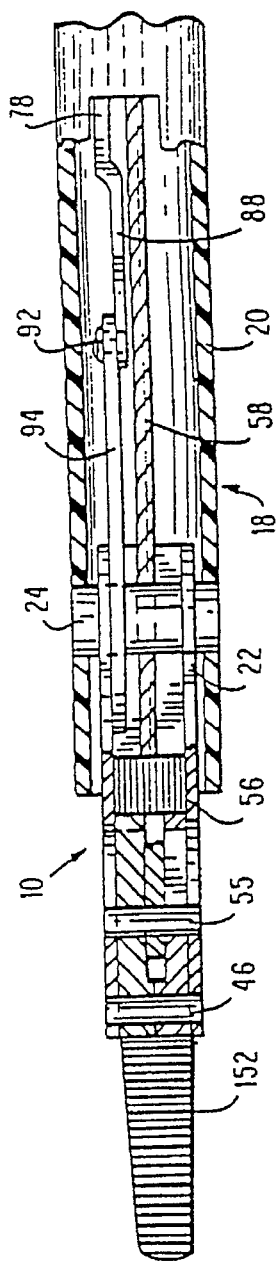
FIG. 12 is a top cross-sectional view taken along line 12—12 of FIG. 11.
Figure 13:
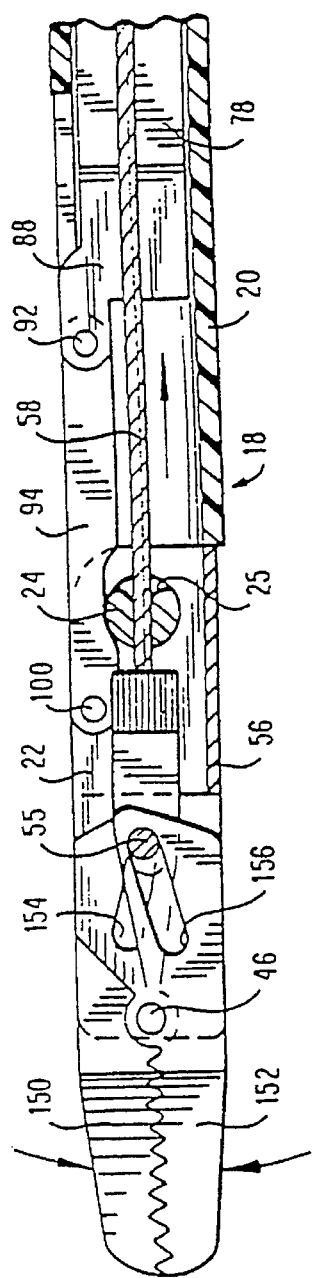
FIG. 13 is a side cross-sectional view of the tool head shown in FIG. 11 in a closed position.

The fixed tubular section 20 of endoscopic portion 18 is formed with a longitudinal slot 42 extending proximally from the distal end 26 thereof. Slot 42 is particularly adapted for enabling the pivotal movement of articulating section 22 about pivot pin 24. An aperture 44 is provided adjacent distal end 26 for maintaining the pivot pin 24. Pivot pin 24 is provided with a transverse diverging bore hole 25, which is best seen in FIG. 4. A circumferential groove 45 is formed in the tubular section 20 adjacent the proximal end 27 thereof for enabling tubular section 20 to be securely mounted in the stepped bore 40 of handle portion 12.

The tool head 28 which depends from articulating section 22 includes cooperating jaws 20, 32, shown here in a clamp configuration. Jaws 30, 32 pivot about a pin 46 which passes through apertures 48, 50 in jaws 30, 32, respectively and through aperture 52 formed in articulating section 22. Jaws 30, 32 also include camming slots 53, 54 respectively formed in the proximal ends thereof for receiving a camming pin 55. Pin 55 is mounted in a yoke 56 and is adapted for reciprocal coaxial movement within the fixed section 20 of endoscopic portion 18. A flexible cable 58 having opposed proximal and distal ends 60 and 62 is mounted, at the distal end 62 thereof, to yoke 56, and at the proximal end 60 thereof, to the distal end 64 of a plunger member 66. Plunger member 66 includes a head portion 68 which is retained in a pivotal clip assembly 70 having opposed complimentary sections 72 and 74. Opposed clip sections 72 and 74 are mounted to one another and are disposed within a port 76 formed in the pivoting handle 16 of handle portion 12. Movements of pivoting handle 16 thus causes corresponding coaxial movements of plunger member 66.

Figure 3:
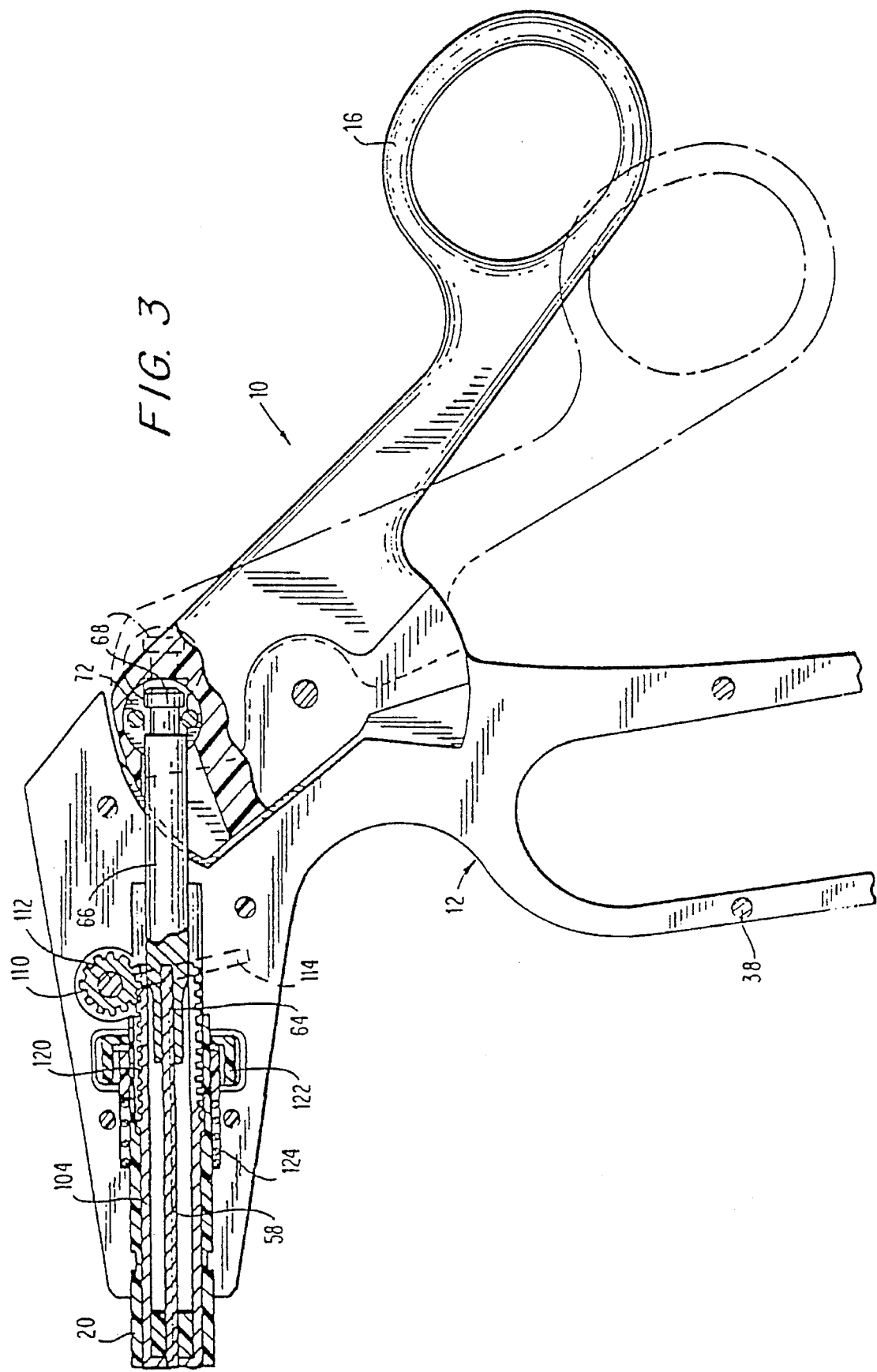
FIG. 3 is a side cross-sectional view taken along line 3—3 of FIG. 1 illustrating the handle portion of the endoscopic instrument.

Referring now to FIGS. 2 and 3, the endoscopic surgical instrument 10 of the subject invention further includes a linkage assembly which is associated with the endoscopic portion 18 and handle portion 12 for pivoting the articulating portion 22 thereof. The linkage assembly includes an elongated push rod 78 having opposed proximal and distal ends 80 and 82, with the proximal end 80 thereof being formed with an aperture 84 for receiving a pin 86. In addition, rod 78 includes a mounting flange 88 provided on the distal end 82 thereof which include an aperture 90 for receiving a pin 92. Pin 92 functions to pivotally connect a link rod 94 to mounting flange 88 through an aperture 96 disposed in the proximal end of link rod 94. Link rod 94 is provided with an aperture 98 in the distal end thereof, through which a pin 100 extends to be pivotally mounted in an aperture 102 which is provided in articulating section 22 of endoscopic portion 18. The linkage mechanism of the subject invention further includes an elongated gear rack member 104 which is capable of being reciprocated in an axial direction. Gear rack member 104 is formed with circumferential gear teeth 106 and an axial bore 107 which is provided to permit flexible cable 58 to extend through so as to reach plunger member 66. Gear rack member 104 is further provided with a mounting flange 108 having an aperture 109. Pin 86 extends through aperture 109 and is mounted in aperture 84 so as to connect rack member 104 to the proximal end 80 of push rod 78. An annular pinion gear 110 is mounted on a shaft 112 associated with handle portion 12. Pinion gear 110 meshes with the circumferential gear teeth 106 on rack member 104. Rotation of pinion gear 110 is achieved by rotating a pair of opposed wing members 114 and 116 which are mounted on the opposed ends of shaft 112.

The endoscopic surgical instrument 10 of the subject invention further comprises a mechanism for rotating the endoscopic portion 18 about its longitudinal axis relative to handle portion 12. This mechanism comprises an annular bushing 120 that is concentrically mounted within a rotatable collar 122 mounted within the stepped bore 40 formed in handle portion 12. Bushing 120 is maintained against collar 122 by a coiled spring 124 disposed in a section of bore 40. Spring 124 acts to bias bushing 120 toward the proximal end of the surgical instrument 10. The proximal end 27 of fixed section 20 of endoscopic portion 18 extends through bushing 120 and is mounted therein for rotation.

Referring to FIGS. 3–6, the operation of the cooperating jaws 30 and 32 of tool head 28 is accomplished by moving the pivoting handle 16 as shown in FIG. 3. Upon moving the pivoting handle 16, the head 68 of plunger member 66 travels axially causing cable 58 to translate. In order to close the cooperating jaws 30 and 32, which are normally open as illustrated in FIG. 4, the pivoting handle 16 is squeezed by the surgeon, thereby causing the plunger member 66 to pull cable 58 in a proximal direction. The movement of cable 58 causes a corresponding axial movement of yoke 56, as shown by the indicator arrow in FIG. 6. In particular, the movement of yoke 56 causes pin 55 to cam proximally within slots 53 and 54 of jaws 30 and 32 respectively, so as to cause jaws 30 and 32 to close. Turning now to FIGS. 7–10, the pivoting movement of the articulating section 22 of endoscopic portion 18 is accomplished by rotating wing members 114 and 116 to a desired angular position. More particularly, a detent engaging member 118 is coaxially mounted on shaft 112 along with wing members 114 and 116 which can rotatably engage in various predetermined positions indicated on handle portion 12 which correspond to 30°, 60°, or 90° of rotation depending upon the surgical procedure being preformed.

To pivot the tool head 28 angularly with respect to the longitudinal axis of the endoscopic portion 18, the wing members 114 and 116 are rotated in a counter clockwise direction. This counter-clockwise rotation causes pinion gear 110 to rotate on shaft 112 in a counter-clockwise direction. Simultaneously, gear rack member 104 advances proximally within stepped bore 40 causing the elongated push rod 78 to advance proximally along the longitudinal axis of endoscopic portion 18. Link member 94 is pulled in a generally proximal direction, a shown by the indicator arrow running parallel to link member 94 in FIG. 7, causing the articulating section 22, and the associated tool head 28, to pivot in an angular direction about pin 24. Once the articulating section 22 is in a desired angular position relative to the longitudinal axis of endoscopic portion 18, the cooperating jaws 30 and 32 may be opened or closed by operating the pivoting handle 16 in handle portion 12 as discussed previously.

Turning now to FIGS. 11–15, an alternate embodiment of the tool head 28 of the endoscopic surgical instrument 10 of the subject invention is illustrated. In this embodiment, the tool head 28 includes cooperating dissector jaws 150, 152 which are pivotally mounted on the articulating section 22 of endoscopic portion 18. Furthermore, dissector jaws 150, 152 are provided with camming slots 154, 156 respectively formed in the distal ends thereof. As in the preferred embodiment, camming pin 55 is accommodated within slots 154, 156 and slides in response to axial movements of yoke member 56 when the pivoting handle 16 is operated to open and close jaws 150 and 152.

Referring to FIGS. 14 and 15, when link rod 94 is moved in a generally proximal direction, tool head 28 pivots relative to the longitudinal axis of endoscopic portion 18. Upon reaching a desired angular position, the cooperating dissector jaws 150 and 152 may be opened or closed by operating pivoting handle 16 of handle portion 12. Moreover, when pivoting handle 16 is operated, cable 58, which extends through the diverging bore 25 formed in pivot pin 24, pulls on yoke member 56 causing pin 55 to slide within slots 154 and 156, thereby opening or closing the dissector jaws 150 and 152.

Turning now to FIG. 16, an alternate endoscopic surgical instrument 200 of the subject invention is illustrated. Surgical instrument 200 comprises a handle portion 202 configured as a pistol-grip, and an endoscopic portion 204. Endoscopic portion 204 includes a fixed tubular section 206 having opposed distal and proximal ends 208 and 210, and an articulating section 212 which is pivotally connected to the fixed section 206 by a pivot pin 214 disposed adjacent to the distal end 208 thereof. Surgical instrument 200 further comprises an elongated paddle 216 which depends from articulating section 212 and which is intended for use as a retractor tool during surgical procedures.

An electrocautery connecter 213 is provided and extends from the handle portion 202 for cauterization of tissue at the surgical site during the surgical procedure. The connector 213 is in electrical connection with the tool 216. In order to protect the surgeon who is using the device from electrical shock, the handle 202 is preferably constructed of a rigid non-conducting material which renders the apparatus lightweight and electrically insulated.

Referring to FIG. 17, surgical instrument 200 is provided with a linkage assembly that is similar to the assembly provided in the preferred embodiment of the subject invention. It comprises an elongated push rod 218 which is pivotally connected to a link member 220 by a pin 222. Link member 220 is pivotally connected to articulating section 212 by a pin 224. Referring to FIG. 18, the linkage assembly also includes an annular pinon gear 226 which is mounted for rotation on a shaft 228 provided in handle portion 202. Wing members 230 are coaxially mounted on shaft 228 for rotating pinon gear 226. Pinon gear 226 meshes with a reciprocating gear rack member 232 disposed within the stepped bore 234 which is formed in handle portion 202. Furthermore, gear rack member 232 is connected to elongated push rod 218.

Surgical instrument 200 also includes an assembly for rotating the endoscopic portion 204 about its longitudinal axis. The rotating assembly includes an annular collar 236 which is disposed within a port 238 formed in bore 234, and an annular bushing 240 concentrically disposed within the annular collar 236. Bushing 240 is provided for accommodating the proximal end of endoscopic portion 204, which is mounted therein for rotation. A coiled spring 242 is disposed within stepped bore 234 for biasing bushing 240 in a proximal direction so as to maintain it within collar 236.

Referring now to FIG. 19, to lower the retractor paddle 216 into a position parallel to the longitudinal axis of endoscopic portion 204, the wing members 230 are rotated in a clockwise direction. This clockwise rotation of wing members 230 causes a clockwise rotation of pinion gear 226 about shaft 228. Consequently, gear rack member 232 is caused to advance distally along the axis of endoscopic portion 204. Push rod 218 advances distally within the fixed section 206 of endoscopic portion of 204. Upon advancing, push rod 218 causes link member 220 to move in a generally distal direction, thereby causing paddle 216 to pivot downwardly, as shown by the indicator arrow in FIG. 19.

Figure 20:
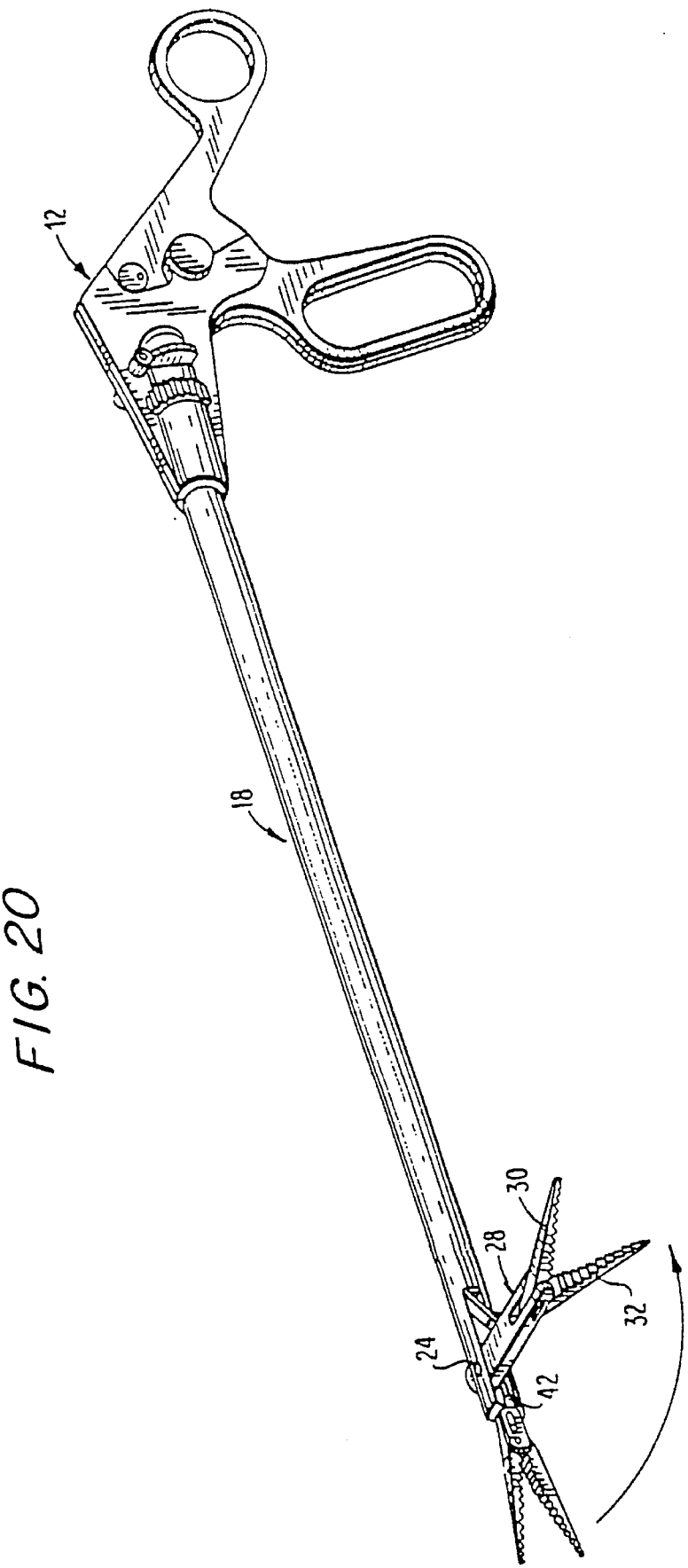
FIG. 20 is a perspective view of another embodiment of the articulating endoscopic surgical instrument of the subject invention.
Figure 21:
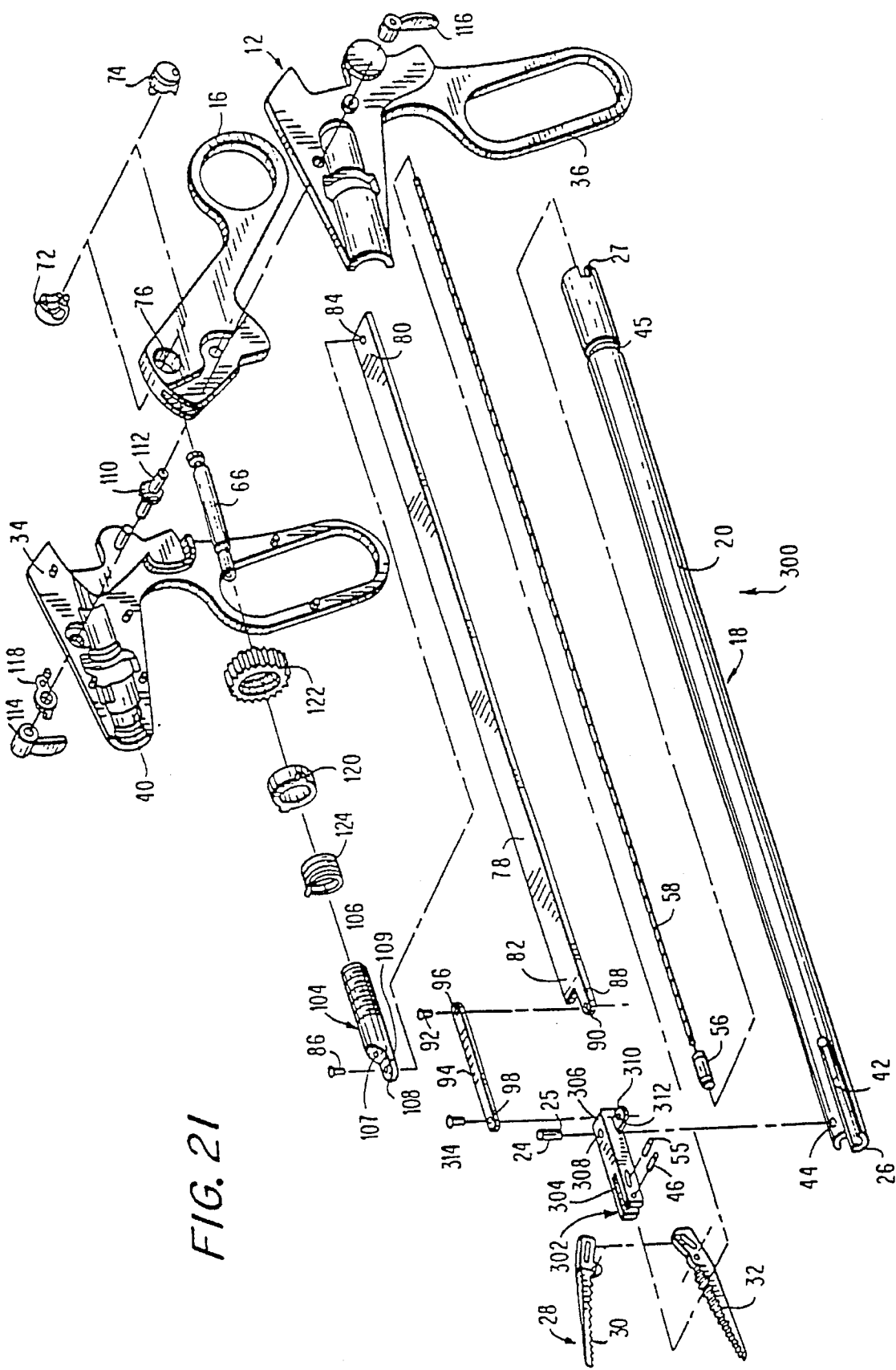
FIG. 21 is an exploded view of the articulating endoscopic surgical instrument of FIG. 20.

Turning to FIGS. 20 and 21, an alternative endoscopic surgical instrument 300 of the subject invention is illustrated. Surgical instrument 300 is structurally similar to the preferred embodiment of the subject invention. However, the range of operability of the tool head 28 of surgical instrument 300 is distinct in that it can be pivoted in a horizontal plan with respect to the endoscopic portion 18 of surgical instrument 300.

In this embodiment, the components and function of the linkage assembly remains essentially the same as in the preferred embodiment. In particular, annular pinion gear 110 which is mounted on a shaft 112 in handle portion 12, meshes with the circumferential gear teeth 106 of gear rack member 104. The proximal end 80 of the elongated push rod 78 is pivotally connected to the flange 108 of gear rack member 104 and the distal end 82 of the elongated push rod 78 is pivotally connected to link member 94 by a pin 92. The linkage assembly of surgical instrument 300 is operatively connected to an articulating section 302. Articulating section 302 includes a slotted distal portion 304 and a proximal portion 306 having a bore 308 for receiving pivot pin 24. A cleat 310 extends outwardly from the proximal portion 306 of articulating section 302 and includes an aperture 312 for receiving a pivot pin which connects the link member 94 to the articulating section 302.

To pivot the tool head 28 angularly, in a horizontal plane, with respect to the longitudinal axis of the endoscopic portion 18, the wing members 114 and 116 are rotated. Simultaneously, gear rack member 104 advances within stepped bore 40 causing the elongated push rod 78 to advance along the longitudinal axis of endoscopic portion 18. Movement of the elongated push rod 78 causes link member 94 to pivot in such a manner so as to cause the articulating section 302, and the associated tool head 28, to pivot in an angular direction about pivot pin 24. Once the articulating section 302 is in a desired angular position relative to the longitudinal axis of endoscopic portion 18, the cooperating jaws 30 and 32 may be operated by manipulating the pivoting handle 16 in handle portion 12 as discussed hereinabove.

Figure 22:
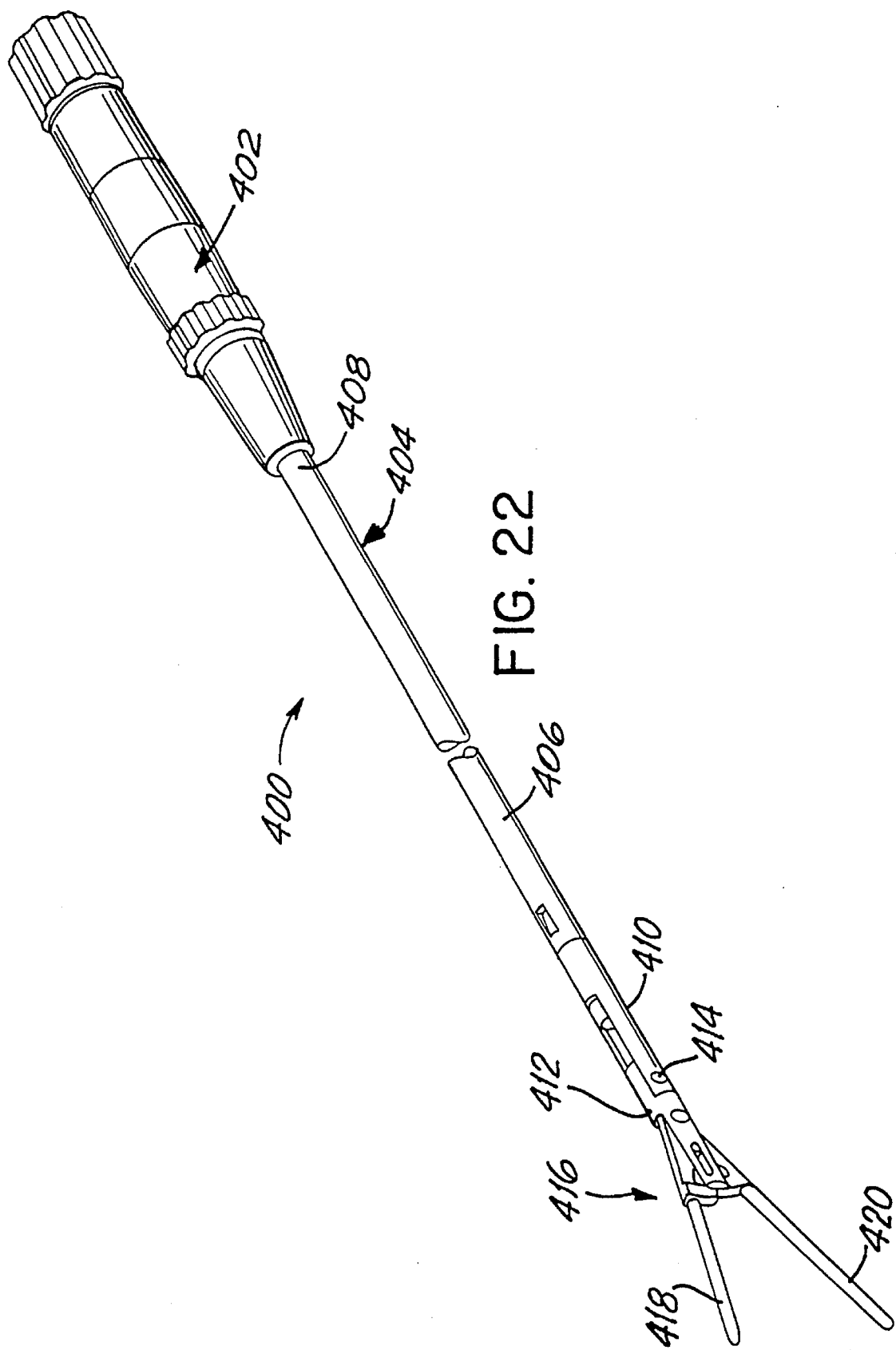
FIG. 22 is a perspective view of another embodiment of the articulating endoscopic surgical instrument of the subject invention adapted for gynecological procedures.

Referring to FIG. 22, another endoscopic surgical instrument 400 of the subject invention is illustrated which may be used as a retractor during gynecological procedures and particularly as an intrauterine retractor. Surgical instrument 400 comprises a substantially barrel shaped axial handle portion 402, and an elongated endoscopic portion 404 which extends outwardly from handle portion 402. Endoscopic portion 404 includes a tubular section 406 by a pivot pin 414 adjacent the distal end portion 410 thereof. A retractor assembly 416 is operatively associated with the articulating section 412 of endoscopic portion 404 and includes a pair of cooperating atraumatic rod members 418 and 420 each having cylindrical bodies with blunt heads configured so as not to cause damage to tissue during retraction procedures.

Figure 23:
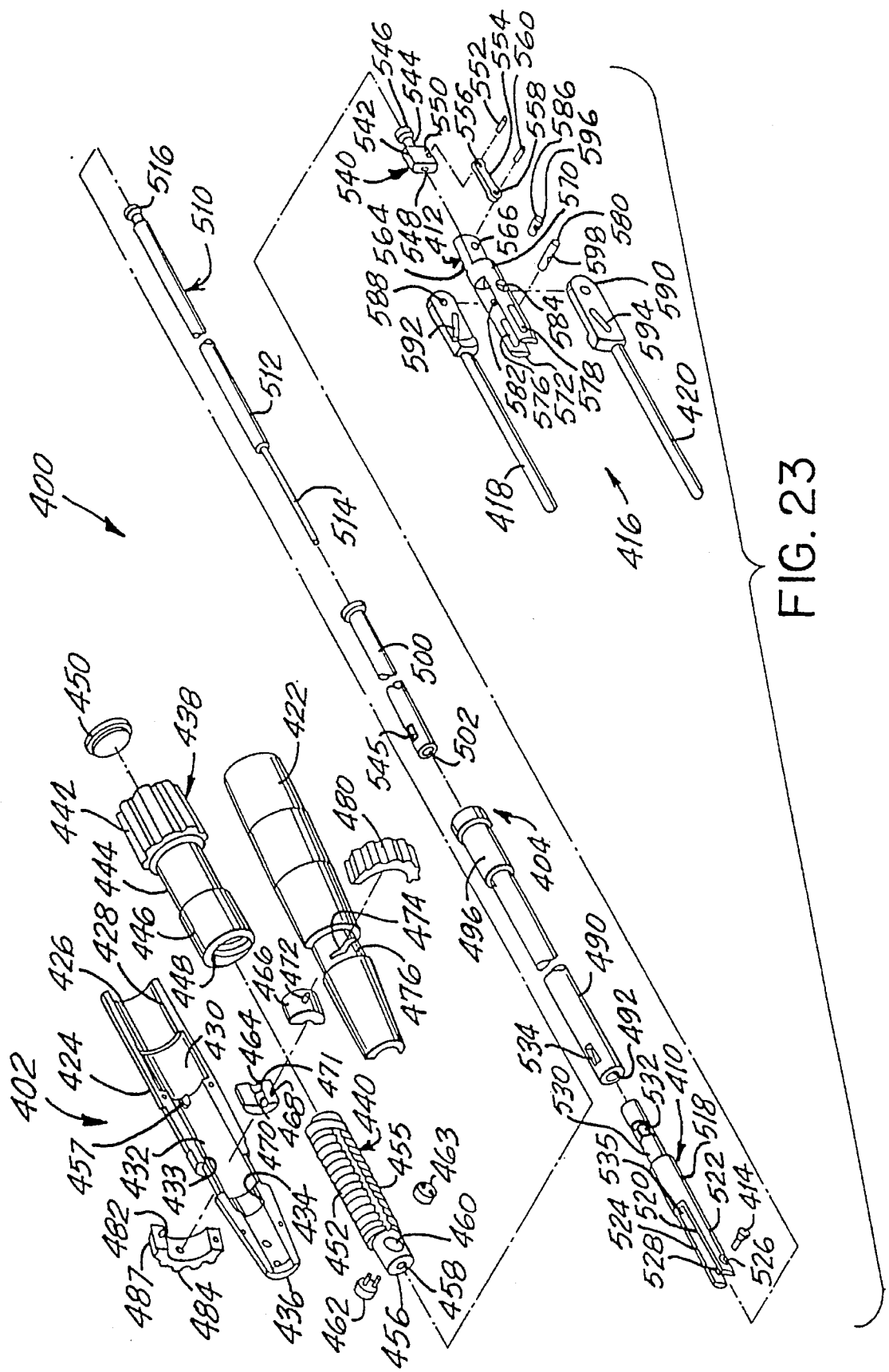
FIG. 23 is an exploded perspective view of the articulating endoscopic surgical instrument of FIG. 22.

Turning to FIG. 23, the handle portion 402 of surgical retractor 400 includes a two-part handle having right and left mountable hemi-sections 422 and 424. Once assembled, the hemi-sections 422 and 424 a stepped axial bore 426 which extends through the handle portion 402. The axial bore 426 has a proximal chamber 428, a primary medial chamber 430, a secondary medial chamber 432, a tertiary medial chamber 433, a quaternary medial chamber 434, and a distal chamber 436 defined therein. The handle portion 402 houses, within the axial bore 426, a driving assembly which manipulates the retractor assembly 416, and a camming assembly which manipulates the articulating section 412 of endoscopic portion 404.

The driving assembly of surgical instrument 400 includes knob member 438 and an associated threadably advanceable driving screw member 440. Knob member 438 comprises a proximal grasping portion 442, an intermediate cavity portion 444, and a distal engaging portion 446. A threaded axial bore 448 extends at least partially through the knob member 438 from the distal engaging portion 446 thereof to the proximal grasping portion 442 where it is capped by a threaded closure member 450. Knob member 438 is mounted within the axial bore 426 of handle portion 402 in such a manner so that the distal engaging portion 446 thereof is maintained within the primary medial chamber 430 of axial bore 426 which the intermediate cavity portion 444 is maintained within the proximal chamber 428 of axial bore 426. Once mounted, knob member 438 is rotatable about the longitudinal axis of handle portion 402.

The driving screw member 440 of the driving assembly comprises an elongated threaded body portion 452 having a proximal end portion 454 which engages operatively within the threaded axial bore 448 of knob member 438, and a distal head portion 456 which extends from the threaded body potion 452 thereof. Lateral slots extend along the body portion 452 of screw member 440 for cooperatively engaging protuberances 457 projecting radially into the secondary medial chamber 432 of axial bore 426. The engagement of the protuberance 457 within lateral slot 455 prohibits rotational movement of screw member 440 when the knob member 438 is rotated and in addition, provides guidance for the screw member 440 within the axial bore 426.

A bore 458 extends axially into the distal head potion 456 of the driving screw member 440 for permitting retention of elements of endoscopic portion 404 therein. A transverse aperture 460 is provided in the head portion 456 of screw member 440 for accommodating a two-part universal locking clip 462, 463 which engages an element of endoscopic portion 404 extending into bore 458. Once mounted within the handle portion 402, the threaded body portion 452 of screw member 440 is maintained partially within the secondary medial chamber 432 of axial bore 426. Rotations of the knob member 438 relative to the handle portion 402 will cause corresponding axial translation of the driving screw member 440 within the secondary medial chamber 432 of axial bore 426 in handle portion 402.

The camming assembly for manipulating the articulating section 412 of endoscopic portion 404 includes a cylindrical cam follower having right and left hemi-portions 464 and 466 mountable to one another by bosses such as, for example, boss 468 on right hemi-portion 464. An axial pathway 470 is formed in the cylindrical cam follower 464, 466 for accommodating elements of endoscopic portions 404. In particular, an annular groove 471 is formed therein for engagement purposes. A cam follower post 472 projects radially outward from the periphery of left hemi-potion 466 and travels within cam slot 474 formed in the left hemi-section 422 of handle portion 402. The cam slot 474 is disposed within a circumferential groove 476 defined in the outer surface of handle portion 402 external from the tertiary medial chamber 433 of axial bore 426.

The cylindrical cam follower 464, 466 is adapted and configured to move axially and rotatably within the tertiary medial chamber 433 of stepped axial bore 426 in response to rotation of a two-part manipulating collar having right and left hemi-portions 478 and 480 mountable to one another by mounting projections, such as, for example, mounting projection 482. An aperture 484 extends radially through hemi-portion 478 of the manipulating collar for receivably engaging the cam follower post 472 so as to operatively interlock the elements of the camming assembly. Rotation of collar 478, 480 will cause cam post 472 to be driven in a cam slot 474 causing axial advancement of the camming assembly relative to the handle portion 402.

The endoscopic portion 404 of surgical instrument 400 extends from handle portion 402, and comprises a plurality of coaxial tubular members including an outer tubular member 490 having an axial bore 492 a stepped proximal end which defines a first annular ridge portion 494, and a second annular ridge portion 496 for mounting the endoscopic portion 404 to handle portion 402. The first annular ridge portion 494 is maintained in the quantenary medial chamber 434 of axial bore 426, while the second annular ridge portion 496 is maintained in the distal chamber 436 of axial bore 426 for mounting the endoscopic portion 402 to handle portion 402.

Endoscopic portion 404 also includes an inner tubular member 500 having an axial passageway 502, and a proximal annular mounting flange 504 dimensioned for locking engagement in the annular groove 471 of the axial bore 470 in cylindrical cam follower 464, 466. An internal control member 510 extends through the axial passageway 502 of inner tubular member 500 and includes an outer sleeve 512, and a central rod 514. Central control rod 514 has a proximal tail portion 516 which is engagable within the distal head portion 456 of screw member 440 by the two-part universal clip 462, 463 such that axial translation of screw member 440, in response to rotations of knob member 438, will cause corresponding axial translation of the center control rod 514 within endoscopic portion 404. A distal end portion 515 of central control rod 514 is flexible for permitting operation of the retractor assembly 416 when the articulating section 412 is pivoted into an operative position.

The distal end portion 410 of endoscopic portion 404 defines a sleeve member which includes a yoke portion 518 having a longitudinally extending slot 520 provided therein defining a pair of opposed depending arms 522 and 524 for accommodating pivotal movement of the articulating section 412 relative to endoscopic portion 404. Apertures 526 and 528 are respectively provided in the opposed depending arms 522 and 524, and a tail portion 530 extends proximally from the yoke portion 518 thereof with a circumferential groove 532 provided therein. A tang 534 is formed adjacent the distal end of the outer tubular portion 490 for lockingly engaging the circumferential groove 532 in tail portion 530 of yoke portion 518 when it is extended into the axial bore 492 thereof to connect the distal end portion 419 to the remainder of endoscopic portion 404. In addition, an axial passageway 515 is provided in articulating section 412 for accommodating at least the distal portion road of central control rod 514.

Surgical instrument 400 further comprises a linkage mechanism for moving the articulating section 412 of endoscopic portion 404 within a defined angular degree of rotation. The linkage mechanism includes a base link 540 having a body portion 542 and a tail portion defined by an intermediate circumferential groove section 544 and a proximal annular section 546. Base link 540 is secured within the axial passageway 502 of inner tubular portion 500 by a tang 545 formed adjacent the distal end of inner tubular portion 500, and configured for engaging the circumferential groove section 544 thereof. A central passageway 548 extends through base link 540, adjacent the lower edge thereof, for accommodating a proximal pivot pin 552 which inter links the base link 540 with a connective link 554 through a proximal aperture 556 provided therein. A distal aperture 558 is also provided in connective link 554 for accommodating distal pivot pin 560 which is received in a corresponding aperture 562 provided in the proximal portion 564 of articulating section 412 adjacent the lower edge thereof, Thus, connective link 554 functions to interlink the articulating section 412 to the base link 540 of the linkage mechanism.

The articulating section 412 of endoscopic portion 404 has a centrally disposed transverse aperture 566 formed in the proximal portion 564 thereof for accommodating the main pivot pin 414. A longitudinal aperture 570 extends through the articulating section 412 for permitting extension of the central control rod member 514 therethrough. Articulating section 412 further includes opposed depending yoke arms 572 and 574 each having an aligned longitudinal cam slots 576 and 578 formed therein respectively, for cooperating with a cam follower pin 580. In addition, opposed aligned pivot ports 582 and 585 are provided in the lateral yoke arms 572 and 574, respectively.

The cooperating atraumatic retractor rod members 418 and 420 are pivotably connected to the opposed lateral yoke arms 572 and 574 of articulating section 412 by engagement of a pivot pin 586 within the opposed pivot ports 582 and 584, and also within corresponding pivot ports 588 and 590 provided in the retractor rod members 418 and 420, respectively. Symmetrically disposed angular camming slots 592 and 594 are also formed in retractor rod member 418 and 420 respectively, for working with cam follower pin 580. A transverse bore 596 is provided in pivot pin 586 for permitting a portion of the distal end 515 of central control rod 514 therethrough, and a transverse bore 598 is provided in camming pin 580 for receivably engaging a distal end portion of central control rod 514.

The termination of the distal portion 515 of central control rod 514 within camming pin 580 achieves complete connectivity between the driving assembly in handle portion 402 and the retractor assembly 416 of endoscopic portion 404. Moreover, axial movements of the central control rod 514, in response to axial translation of driving screw 440, will cause corresponding cooperative movement of the retractor rod members 418 and 420 through the translation of camming pin 580 relative to the angular cam slots 592 and 594.

Referring now to FIGS. 24–26, the surgical instrument 400 may advantageously be employed as a retractor during gynecological procedures by rotating the knob member 438 counterclockwise (as viewed from the proximal end of the instrument) to move the cooperative retractor rod members 418 and 420 from the closed position of FIG. 24, to the opened position of FIG. 25. More particularly, upon rotating knob member 438 counterclockwise, the drive screw member 440 will translate in the direction of arrow "C". As screw member 440 retreats, the tail portion 516 of the central control rod 514 is pulled in a proximal direction causing the camming pin 580, which is fixed to the distal end thereof, to move proximally within the angled camming slots 592 and 594 of rod members 418 and 420. Distal movement of camming pin 580 within camming slots 592 and 594 causes the cooperating retractor rod members 418 and 420 to open in the direction of arrow "B". Closure of rod members 418 and 420 is achieved through counter rotation of knob member 438. Transposition of the rotation from counterclockwise to clockwise for purposes of deploying the retractor assembly is also with the scope of the invention.

Turning now to FIG. 26, in operation, the articulating section 412 of endoscopic portion 404 may be pivoted in the direction of arrow "E" within a vertical plane with respect to the longitudinal axis of endoscopic portion 404 into various angularly disposed positions. To achieve this articulated movement, the manipulating collar 476, 478 is rotated clockwise (as viewed from the proximal end of the instrument, causing cylindrical cam follower 466, 468 to rotate concomitantly therewith. As a cam follower 466, 468 rotates, the cam post 472 translates within the cam slot 474 from a first position, best seen in FIG. 24, wherein collar 478 is in its proximal most position within circumferential groove 476, to a second position, best seen in FIG. 25, wherein collar 478 is in its distalmost position within groove 476. The axial translation of cylindrical cam follower 464, 466 causes the inner tubular portion 500 of endoscopic portion 404 to move in a distal direction, since the proximal flange 504 of inner tubular portion 500 is engaged in the groove 471 defined in passageway 470 of cam follower 464, 466. As inner tubular portion 504 moves distally, it extends outwardly from the axial bore 535 in the sleeve member defined by the distal portion 410 of endoscopic portion 404, such that base link 540 is urged distally within the slotted area 520 of distal portion 410. Thereupon, connective link 554 is urged in a generally distal direction, pivoting about pivot pins 552 and 560, and causing the articulating section 412 to be pivoted angularly with respect to the longitudinal axis of endoscopic portion 404 about the main pivot pin 414.

The angle of vertical translation of articulating section 412 can vary depending upon the degree of rotation of manipulating collar 478. In addition, once in an articulated position, the retractor assembly 416 can be manipulated independently, since the distal end portion 515 of the central control rod 514 is substantially flexible, as seen in FIG. 26. Transposition of the rotation from clockwise to counter-clockwise for articulating the instrument is also within the scope of the invention.

Figure 27:
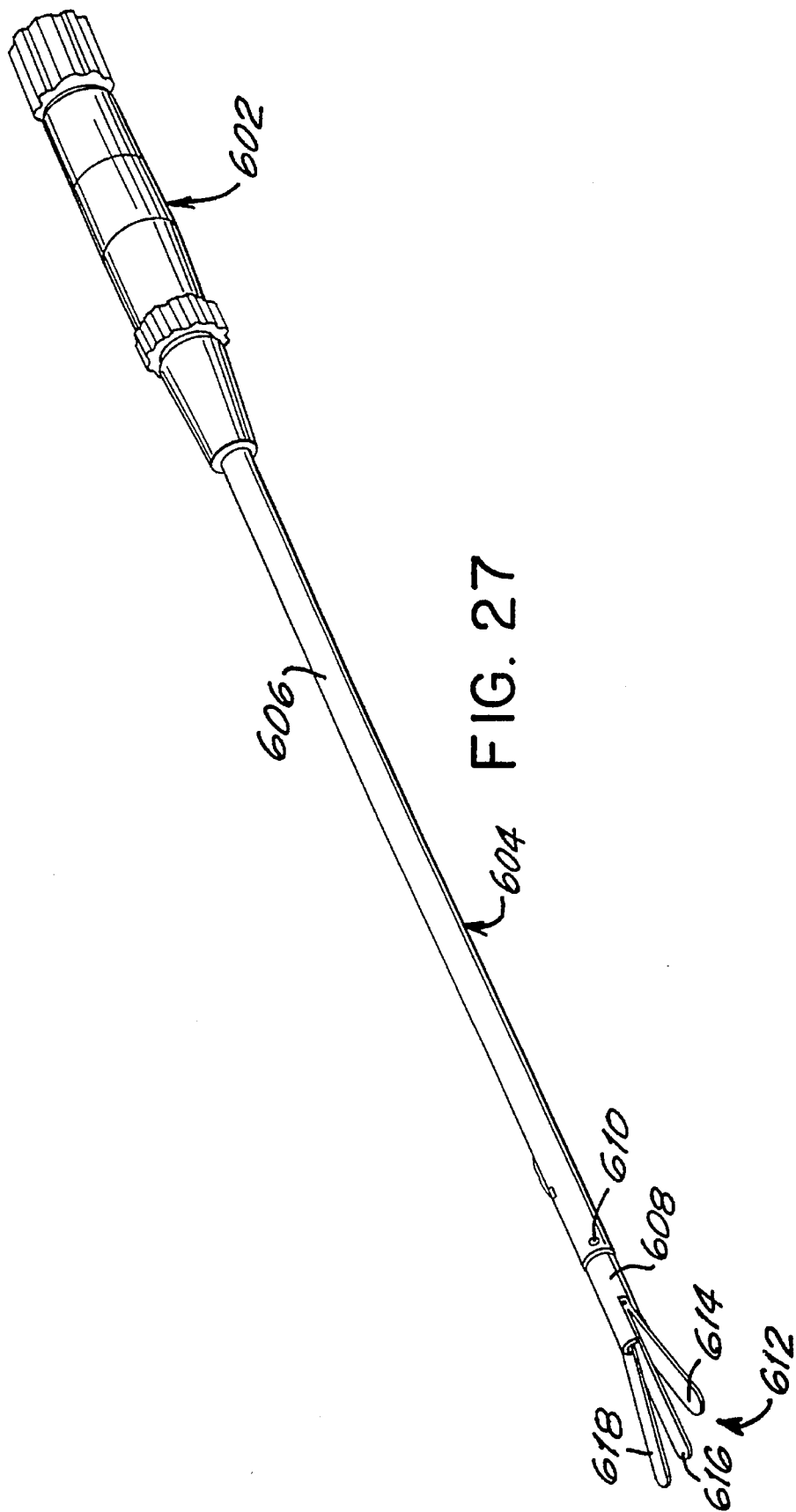
FIG. 27 is a perspective view of yet another embodiment of the endoscopic surgical instrument of the subject invention.

Turning to FIG. 27, yet another embodiment 600 of the articulating surgical retractor of the subject invention is illustrated which may be used endoscopically or during laparoscopic procedures within the abdominal cavity. Surgical instrument 600 comprises an axial handle portion 602, and an elongated endoscopic portion 604 extending from the axial handle portion 602 and including an elongated tubular section 606, and an articulating distal section 608 pivotably connected to the elongated tubular section 606 adjacent the distal end thereof by a main pivot pin 610. A retractor assembly 612 is operatively associated with the articulating section 608 and includes a plurality of cooperative interleaved retractor blade members 614, 616, and 618.

Figure 28:
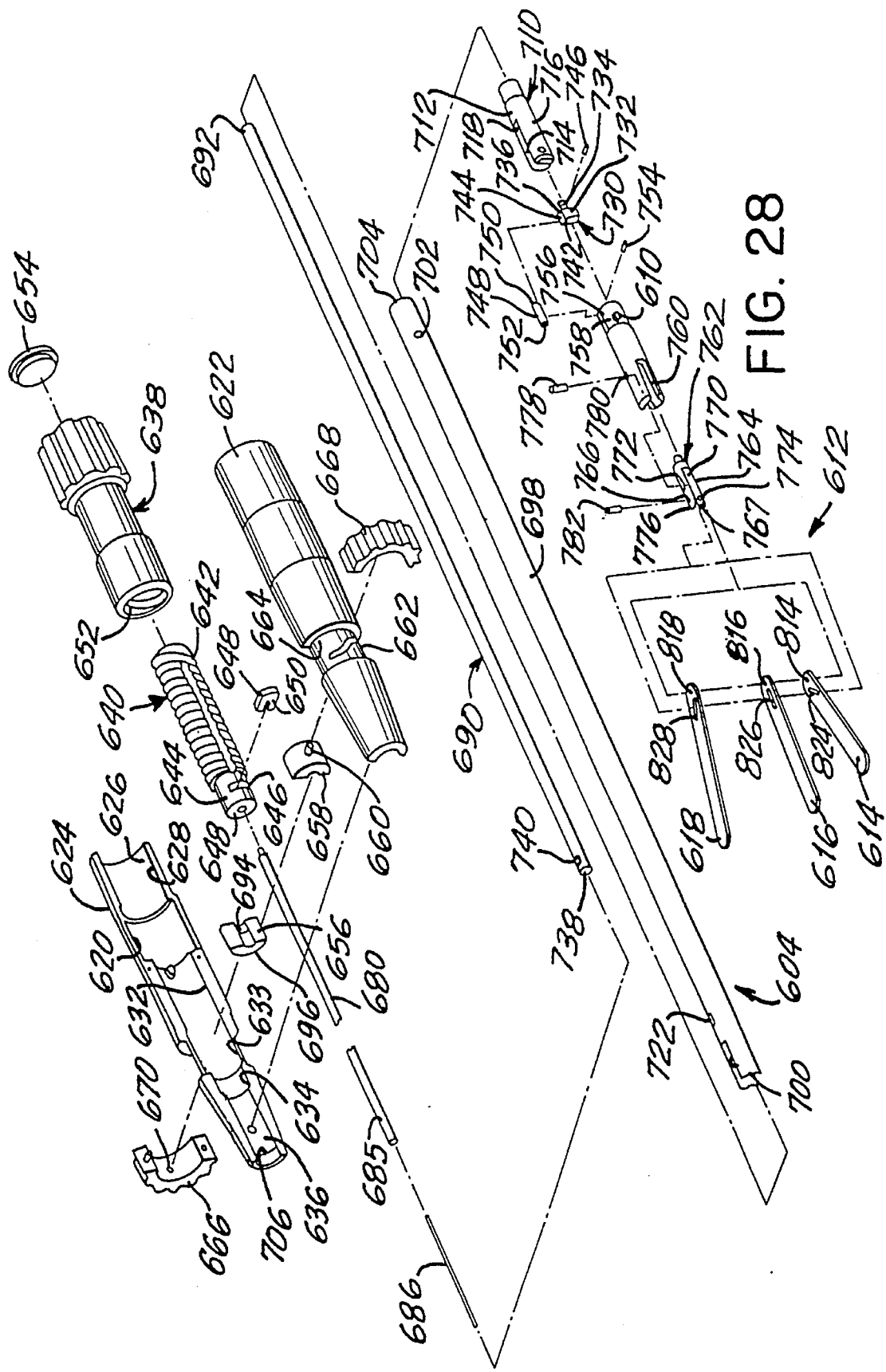
FIG. 28 is an exploded perspective view of the articulating endoscopic surgical instrument of FIG. 27.

Referring to FIG. 28, the handle portion 602 of surgical instrument 600 is substantially identical to that of surgical instrument 400. It comprises mountable right and left hemi-sections 622 and 624 having a stepped axial bore 626 extending therethrough defined by a proximal chamber 628, a primary medial chamber 630, a secondary medial chamber 632, a tertiary medical chamber 633, a quaternary medial chamber 634, and a distal chamber 636. The handle portion 602 houses, within the axial bore 626, a driving assembly for manipulating the retractor assembly and a camming assembly for manipulating the articulating section 608 of endoscopic portion 604.

The driving assembly includes a rotatable knob member 638 and an axially advanceable driving screw 640. Driving screw 640 varies from the driving screw 440 of surgical instrument 400 in that it includes a body portion 642 having a distal head portion 644 provided with a transverse slot 646 for accommodating a transverse planar engaging clip 648. Engaging clip 648 is formed with a retention notch 650 for lockingly retaining an operative element of endoscopic portion 604. The knob member 638 is formed with an internal threaded bore 652 extending at least partially therethrough for operatively engaging the driving member 640, and which is covered by closure member 654.

The camming assembly includes a cylindrical cam follower having mountable right and left hemi-sections 656 and 658 configured for rotational and axial movement within the tertiary medial chamber 633 of axial bore 626. A camming post 660 extends radially outward from the periphery of left hemi-section 658 and is dimensioned for translating within a cam slot 662 formed in a circumferential groove 664 defined in the outer surface of handle portion 602 external from the tertiary medial chamber 633. A rotatable manipulating collar defined by mountable right and left hemi-portions 666 and 668 is configured for being mounted in circumferential groove 664 and includes a port 670 for receivably engaging the cam post 660 so as to interlock the elements of the camming assembly. Rotation of manipulating collar 666, 668 will cause translation of cam post 660 in cam slot 662, and consequent axial translation of the cylindrical cam follower 656, 658 along the axial center line of the handle portion 602 with the tertiary medial chamber 633.

The endoscopic portion 604 of surgical instrument 600 comprises a central control rod 680 having a tail portion 682 which extends into an axial bore 684 in driving screw member 640 to be lockingly engaged therein by the notch 650 in locking clip 648. In doing so, the axial translation of the driving screw 640 will cause corresponding axial movement of the control rod 680. A connective rod 686 is engaged in the distal end 685 of control rod 680 for interconnecting the retractor assembly 612 with the control rod 680. Connective rod 686 is flexible to permit operation of the retractor assembly 612 when the articulating section 608 of endoscopic portion 604 is pivoted into an operative position. Endoscopic portion 604 further comprises an inner tubular portion 690 having an annular flange 692 formed on the proximal end thereof. Flange 692 is dimensioned for engagement in a circumferential groove 694 formed in the axial bore 696 of the cylindrical cam follower 656, 658, such that the inner tubular portion 690 will translate axially when the cylindrical cam follower 656, 658 moves within the tertiary medial chamber 633 of axial bore 626.

The inner tubular portion 690 is disposed within the outer tubular portion 698 which is provided with a longitudinally extending slot 700 in the distal end portion thereof for accommodating the pivotal movements of articulating section 608. A transverse aperture area 702 is defined adjacent the proximal end 704 of the outer tubular portion 698 for receiving a radially inwardly projecting stem 706 disposed in the distal chamber 636 of axial bore 626 in handle portion 602. Engagement of stem 706 in aperture area 702 achieves fixation of the endoscopic portion 604 and the handle portion 602.

A primary yoke member 710 is mountable in the distal end portion of the outer tubular portion 698 which comprises a body portion 712 having a pair of opposed lateral yoke arms 714 and 716 depending therefrom and defining a slotted area 718 therebetween. A circumferential groove 720 is provided in the body portion 712 for being engaged by a locking tang 722 formed adjacent the slotted area 700 in the outer tubular portion 698. Opposed pivot ports, of which 724 is one, are defined in the opposed lateral yoke arms 714 and 716 for accommodating main pivot pin 610 which is formed integral with the articulating section 608 of endoscopic portion 604.

A linkage assembly interlinks the articulating section 608 with the inner tubular portion 690 of endoscopic portion 604. The linkage assembly includes a base link 730 having a body portion 732 from which extends a proximal tail portion 734 provided with a circumferential groove 736. The tail portion 734 is adapted to be extended into the distal end 738 of inner tubular portion 690 and is maintained therein by a locking tang 740 which is engagable in the circumferential groove 736. An axial bore 742 extends through the base link 730 for permitting passage of connective rod 686 therethrough. In addition, an aperture 744 is provided in the body portion 732 of base link 730, adjacent the upper edge thereof, for receiving a proximal pivot pin 746 which interlinks base link 730 with a connective link 748 through a proximal aperture 750 formed therein. Connective link 748 has a distal aperture 752 for receiving a distal pivot pin 754 which is provided for interlinking connective link 748 with the articulating section 608 of endoscopic portion 604 through an aperture 756 provided in the proximal end portion 758 of articulating section 608. Axial translation of the inner tubular portion 690, in response to movement of the camming assembly, will cause the corresponding translation of the base link 730 within the slotted portion 718 of primary yoke member 710, whereby the connective link 748 will move generally axially to cause pivoting movement of articulating section 608 in a vertical plane relative to the longitudinal axis of the endoscopic portion 604 of surgical instrument 600.

The articulating section 608 of endoscopic portion 602 is formed with a slotted area 760 for accommodating the retractor assembly 612 of surgical instrument 600. The retractor assembly 612 includes a secondary yoke member 762 having opposed upper and lower yoke arms 764 and 766 defining a slotted retractor blade maintaining area 768 therebetween. Opposed longitudinally extending guide slots 770 and 772 are provided in upper and lower yoke arms 764 and 766, respectively, as well as opposed pivot apertures 774 and 776, respectively. A guide pin 778 extends through a maintaining aperture 780 in the articulating section 608, and into the opposed guide slot 770 and 772, while a camming pin 782 extends through the opposed pivot apertures 774 and 776. Guide pin 778 and camming pin 782 both cooperate with the interleaved retractor blades 614, 616, and 618. More particularly, corresponding pivot ports 814, 816 and 818 are provided respectively in the interleaved retractor blade 614, 616, and 618, for receiving guide pin 778. Retractor blades 614, 616 and 618 are made of a suitable surgical material having sufficient strength for the desired retractor function. Such materials include stainless steel, plastics and/or combinations thereof. Camming slots are provided in the retractor blades for working with camming pin 782, and include an angularly disposed camming slot 824 formed in retractor blade 614, a longitudinally disposed camming slot 826 formed in retractor blade 616, and an angularly disposed camming slot 828 formed in retractor blade 618. Camming slots 824 and 828 are arranged in symmetrical relationship, such that translation of the camming pin 782, in response to movements of secondary yoke member 762, will cause a fan-like deployment of the interleaved retractor blades 614, 616, and 618.

Referring to FIGS. 29–32, in use, the retractor blade assembly 612 is moved from the closed position illustrated in FIG. 29, to an opened position illustrated in FIG. 30, by rotating the knob member 638 counterclockwise (as viewed from the proximal end of the instrument) to cause corresponding axial translation of screw member 640 in the direction of arrow "G", within the axial bore 626 of handle portion 602. As driving screw member 640 retreats, the tail portion 682 of the central control rod 680 is pulled proximally, along with the connective rod 686, the distal end of which is fixedly mounted in the proximal end of secondary yoke member 762. At such a time, the opposed guide slots 770 and 772 in secondary yoke member 762 permit relative translation of secondary yoke member 762 in relation to the guide pin 778. Furthermore, as the secondary yoke member 762 is drawn in a proximal direction, camming pin 782 translates proximally within the camming slots 824, 826, and 828 of the retractor blades, causing the interleaved retractor blades 614, 616, and 618 to deploy in a fan-like configuration.

Turning now to FIGS. 31 and 32, to pivot the articulating section 608 of endoscopic portions 604 in the direction of arrow "H" in a vertical plane with respect to the longitudinal axis of endoscopic portion 604 during a surgical procedure, the manipulating collar 666, 668 is clockwise (as viewed from the proximal end of the instrument), such that the cylindrical cam follower 656, 658 is caused to advance from a proximal position to a distal position with the tertiary medial chamber 633 of axial bore 626. At the same time, camming post 660 translates within the camming slot 662 formed in the circumferential groove 664 in handle portion 602. Consequently, the inner tubular portion 690 of endoscopic portion 604 moves in a distal direction, urging the base link 730 distally within the slotted area 718 of primary yoke member 710. Thereupon, connective link 748 is urged in a generally distal direction, causing the articulating section 608 to pivot about main pivot pin 610 in a vertical plane relative to the longitudinal axis of endoscopic portion 604. The angle of vertical translation of articulating section 608 can vary depending upon the degree of rotation of the manipulating collar. Furthermore, while the articulating section 608 is in an angular position, the retractor assembly may be actuated independently, since the connective rod 686 is substantially flexible, as seen in FIG. 32.

FIG. 33 shows an endoscopic surgical retractor 600 substantially the same as that shown in FIGS. 27–32. This retractor 600 is particularly adapted for use in gynecological surgery involving the cervix or uterus. An annular cervical seal 850 is removably disposed on endoscopic portion 604 intermediate the axial handle portion 602 and the articulating distal section 608. This cervical seal 850 assists in preventing the egress of insufflation gases from the uterus during retractor manipulations.

In use, the uterus is insufflated and the retractor is inserted to a point wherein the cervical seal 850 is adjacent the cervix of the patient. In this position the cervical seal 850 inhibits the flow of insufflation gas from the uterus around the exterior of the endoscopic portion 604 of the instrument 600.

Figure 35:
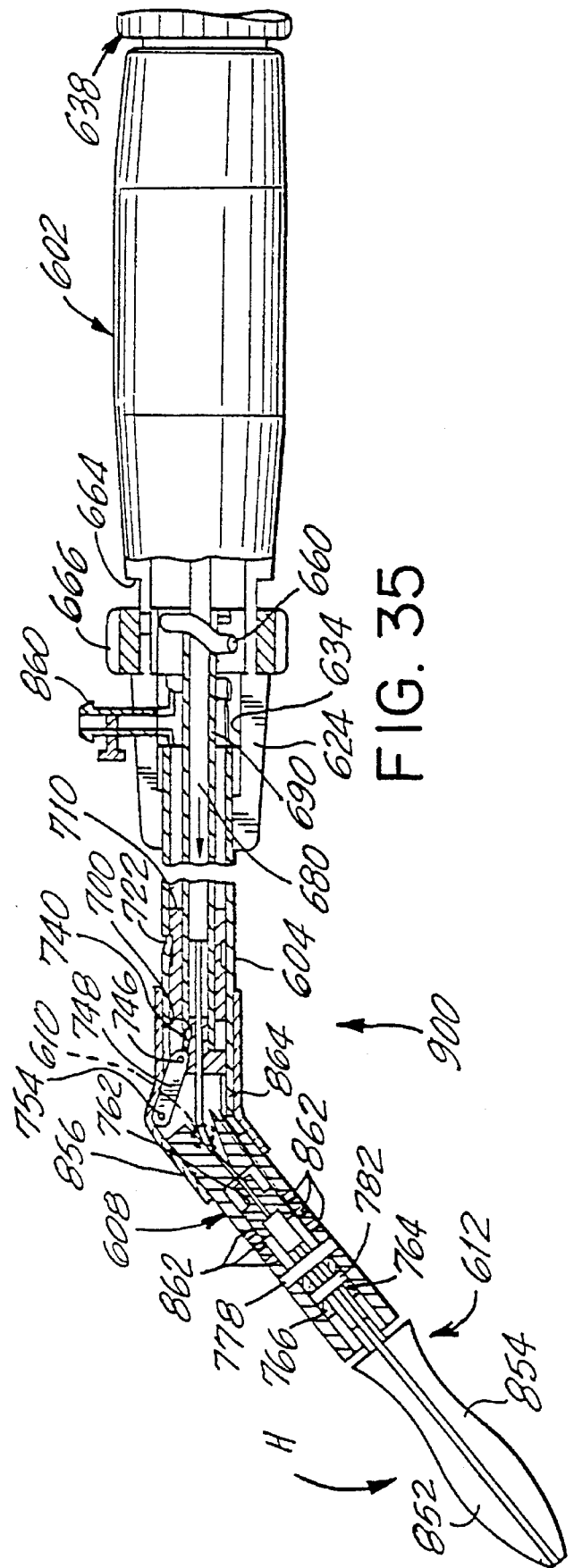

FIGS. 34 and 35 show two alternative embodiments of the endoscopic surgical retractor in accordance with the present invention. These retractors are specifically designed and adapted for gynecological applications and include atraumatic upper and lower blades 852, 854 configured in a streamlined semicircular cross section. In the retracted configuration, the blades interleave to form a smooth rounded retractor assembly for atraumatic insertion, particularly when used without a cannula port.

The endoscopic surgical retractors shown in FIGS. 34 and 35 are also provided with a sleeve 856 extending around the distal end of the endoscopic portion 604 and the proximal end of the articulating portion 608. This sleeve 856 serves to enclose and protect the articulating linkages from external contamination. Also, the sleeve 856 prevents tissue or organs from becoming entangled in the linkages during operation. The sleeve 856 is preferably formed of an elastic or silastic material capable of moving with the articulating portion 608.

Referring specifically to FIG. 34, the endoscopic surgical retractor includes an injection port 858 disposed adjacent a distal end of the handle portion 602. The injection port 858 communicates with the interior of the endoscopic portion 604 to permit fluid to be injected therethrough into the surgical site. The injection port 858 of the retractor in FIG. 34 comprises a substantially inverted "T" structure providing direct access to the passages in the endoscopic portion 604. This structure may advantageously be used for fluid irrigation or medication of the operative site. Alternatively, the port may be used to administer dyes or marker substances intravaginally such as, for example, radiopaque dyes injected to determine the patency of the fallopian tubes, etc. Where a surgical retractor having an injection port feature is to be used in an insufflated cavity, valve 866 is positioned in line to inhibit insufflation gases from exiting the cavity through the port.

The endoscopic surgical retractor of FIG. 35 is substantially the same as the retractor of FIG. 34 except that the injection ports 860 communicates with a plurality of distribution ports 862 through tube 864 disposed coaxially in endoscopic portion 604. This configuration allows for more accurate delivery of fluids and may even be used to administer pressurized aerosols therethrough. The endoscopic surgical instrument of the subject invention is compact, lightweight and easy to use. It is intended to enable the surgeon to use the instrument with one hand, thus freeing the other hand for performance of other surgical tasks.

To the extent not already indicated, it also will be understood by those of ordinary skill in the art that any one of the various specific embodiments herein described and illustrated may be further modified to incorporate features shown in other of the specific embodiments.

Although the endoscopic surgical instrument of the subject invention has been described with respect to a preferred embodiment, it is apparent that changes may be made to the invention without departing from the spirit and scope of the invention as defined by the appended claims.

What is claimed is:

1. A surgical apparatus comprising:
   an endoscopic portion including an elongated section having opposed proximal and distal ends;
   an articulating section pivotally connected to a distal end portion of said endoscopic portion;
   tool means connected to said articulating section and including at least two cooperating members movable between a closed position and an open position;
   rotating means cooperating with a proximal portion of said endoscopic portion for moving said at least two cooperating members between said closed position and said open position; and
   a camming assembly cooperating with said proximal portion of said endoscopic portion to effect pivotal movement of said articulating section relative to a longitudinal axis of said endoscopic portion.

2. A surgical apparatus as in claim 1 wherein said tool means comprises a retractor assembly.

3. A surgical apparatus as in claim 1 wherein said moving means includes knob means mounted for rotation relative to said endoscopic portion and driving means threadably associated with said knob means movable in an axial direction in response to rotation of said knob means.

4. A surgical apparatus as recited in claim 2, wherein said retractor assembly includes a pair of atraumatic cooperating rod members.

5. A surgical apparatus as recited in claim 2, wherein said retractor assembly incudes a plurality of interleaved blade members.

6. A surgical apparatus as recited in claim 3, wherein said knob means comprises an elongated knob member having a threaded axial bore extending at least partially therethrough for operatively receiving said driving means.

7. A surgical apparatus as recited in claim 3, wherein said driving means comprises an elongated threaded screw member, and an elongated control rod extending from a distal end of said screw member to said retractor assembly.

8. A surgical apparatus as recited in claim 4, wherein said retractor assembly further includes a yoke member having a set of cam slots, and a camming pin movable within said set of cam slots for cooperating with said pair of cooperating rod members.

9. A surgical apparatus as recited in claim 5, wherein said retractor assembly further includes a yoke member provided with a set of camming slots, and a camming pin movable within said set of cam slots for cooperating with said plurality of interleaved blade members.

10. A surgical apparatus as recited in claim 1, further comprising linkage means associated with said endoscopic portion and extending from said camming assembly to said articulating section.

11. A surgical apparatus as recited in claim 10, wherein said camming assembly includes a cam slot defined in said handle portion and a cam follower associated with said handle portion for translating relative to said cam slot between a proximal position and a distal position.

12. A surgical apparatus as recited in claim 11, wherein said linkage means includes an elongated inner tubular member having a proximal end portion associated with said cam follower and a distal end portion associated with a linkage mechanism interconnecting said articulating section to said camming assembly.

13. A surgical apparatus as recited in claim 12, wherein said linkage mechanism includes a base link connected to said distal end portion of said inner tubular member and a connective link pivotally connected to said base link at one end thereof and to said articulating section at the opposed end thereof.

14. A surgical apparatus comprising:
    an axial handle portion;
    an endoscopic portion extending from said handle portion and defining a longitudinal axis;
    an articulating section pivotally connected to a distal end portion of said endoscopic portion;
    a retractor assembly connected to said articulating section and including a plurality of interleaved blade members movable between a closed position and an open position;
    an actuation knob for moving said plurality of interleaved blade members between said closed position and said open position, said actuation knob mounted for rotation relative to said handle portion, and a drive screw threadably associated with said actuation knob, said drive screw movable in a longitudinal direction in response to rotation of said actuation knob; and
    a camming assembly associated with said handle portion and said endoscopic portion to effect pivotal movement of said articulating section relative to a longitudinal axis of said endoscopic portion.

15. A surgical apparatus as recited in claim 14, wherein said actuation knob comprises an elongated member having a threaded axial bore hole extending at least partially therethrough for operatively receiving said drive screw.

16. A surgical apparatus as recited in claim 14, wherein an elongated control rod extends from a distal end of said drive screw to said retractor assembly.

17. A surgical apparatus as recited in claim 14, wherein said retractor assembly further includes a yoke member provided with a set of camming slots, and a camming pin operatively associated with said camming slots for cooperating with said plurality of interleaved blade members.

18. A surgical apparatus as recited in claim 14, further comprising linkage means associated with said endoscopic portion and extending from said camming assembly to said articulating section.

19. A surgical apparatus as recited in claim 18, wherein said camming assembly includes a cam slot defined in said handle portion and a cam follower disposed in said handle portion for translating relative to said cam slot between a proximal position and a distal position.

20. A surgical apparatus as recited in claim 19, wherein said linkage means includes an elongated inner tubular member having a proximal end portion associated with said cam follower and a distal end portion associated with a linkage assembly interconnecting said articulating section to said camming assembly.

21. A surgical apparatus as recited in claim 20, wherein said linkage mechanism includes a base link connected to said distal end portion of said inner tubular member and a connective link pivotably connected to said base link at one end thereof and to said articulating section at the opposed end thereof.

22. A surgical apparatus comprising:
  (a) an axial handle portion;
  (b) an endoscopic portion extending axially from said handle portion;
  (c) an articulating section pivotably connected to a distal end portion of said endoscopic portion;
  (d) a retractor assembly operatively associated with said articulating section and including at least two cooperating retractor members movable between a closed position and an open position;
  (e) a first actuator for moving said at least two cooperating retractor members between said closed position said open position, said first actuator including;
    (i) a knob member mounted for rotation relative to said handle portion;
    (ii) a driving member threadably associated with said knob member for moving axially in response to rotation of said knob member; and
    (iii) an elongated control rod extending from said driving member to said retractor assembly; and
  (f) a second actuator for pivoting said articulating section relative to the longitudinal axis of said endoscopic portion said second actuator including:
    (i) at least one camming member movable with respect to at least one camming slot formed in said handle portion between a proximal position and a distal position; and
    (ii) linkage structure associated with said endoscopic portion for connecting said at least one camming member with said articulating section.

* * * * *